(12) United States Patent
Sereno et al.

(10) Patent No.: US 9,717,459 B2
(45) Date of Patent: Aug. 1, 2017

(54) TOUCH SENSITIVE SYSTEM AND METHOD FOR COGNITIVE AND BEHAVIORAL TESTING AND EVALUATION

(71) Applicant: Anne Bibiana Sereno, Pearland, TX (US)

(72) Inventors: Anne Bibiana Sereno, Pearland, TX (US); Saumil S. Patel, Houston, TX (US); Yujan Shrestha, Houston, TX (US); Stuart Douglass Red, Houston, TX (US)

(73) Assignee: Anne Bibiana Sereno, Pearland, TX (US)

( * ) Notice: Subject to any disclaimer, the term of this patent is extended or adjusted under 35 U.S.C. 154(b) by 247 days.

(21) Appl. No.: 14/192,391

(22) Filed: Feb. 27, 2014

(65) Prior Publication Data

US 2014/0249447 A1    Sep. 4, 2014

Related U.S. Application Data

(60) Provisional application No. 61/772,474, filed on Mar. 4, 2013.

(51) Int. Cl.
  *A61B 13/00* (2006.01)
  *A61B 5/00* (2006.01)
  *A61B 5/16* (2006.01)

(52) U.S. Cl.
  CPC ............ *A61B 5/6898* (2013.01); *A61B 5/162* (2013.01); *A61B 5/7475* (2013.01); *A61B 2560/0487* (2013.01); *A61B 2562/0204* (2013.01)

(58) Field of Classification Search
  CPC ............ A61B 5/16; A61B 3/113; A61B 5/162
  (Continued)

(56) References Cited

U.S. PATENT DOCUMENTS

| 3,946,592 A | 3/1976 | Ichikawa |
| 5,452,363 A | 9/1995 | Mader |

(Continued)

FOREIGN PATENT DOCUMENTS

| WO | WO9932889 A2 | 7/1999 |
| WO | WO2007107618 A1 | 9/2007 |

(Continued)

OTHER PUBLICATIONS

"Response time (technology)," Nov. 9, 2011, Wikipedia.*

*Primary Examiner* — Daniel Cerioni
(74) *Attorney, Agent, or Firm* — James D. Petruzzi; The Petruzzi Law Firm

(57) ABSTRACT

Portable operatively simple touch screen apparatus uses testing methods and systems that are free of age and language constraints include special signal processing techniques that provide a temporal resolution highly sensitive for probing cognitive function. The embodiments include or make use of one or more modules implemented at least partially in a set of instructions in software and configured to measure user reaction times to visual stimulus on a touch screen device having a capacitive sensor touch-sensitive surface and a detector of audio waves resulting from touch on the touch-sensitive surface. The modules employ recordation of acoustic vibrations resulting from a user's touching a target location on the touch screen surface spaced from a touched starting location on that surface, in one embodiment, to measure temporal response to a visual stimulus placed at the target location.

6 Claims, 9 Drawing Sheets

(58) Field of Classification Search
USPC .......................................................... 600/558
See application file for complete search history.

(56) References Cited

U.S. PATENT DOCUMENTS

| | | |
|---|---|---|
| 5,649,061 A | 7/1997 | Smyth |
| 5,767,457 A | 6/1998 | Gerpheide |
| 6,633,280 B1 | 10/2003 | Matsumoto |
| 7,175,598 B2 | 2/2007 | Yoneyama |
| 7,294,107 B2 | 11/2007 | Simon |
| 7,303,399 B1 | 12/2007 | Holdnack |
| 7,720,530 B2 | 5/2010 | Causevic |
| 8,343,066 B1 | 1/2013 | Eagleman |
| 8,519,982 B2 | 8/2013 | Camp |
| 2005/0195216 A1 | 9/2005 | Kramer |
| 2007/0132743 A1 | 6/2007 | Bayramoglu |
| 2009/0270758 A1 | 10/2009 | Eagleman |
| 2010/0164405 A1 | 7/2010 | Devick |
| 2011/0082397 A1 | 4/2011 | Alberts |
| 2011/0084914 A1 | 4/2011 | Zalewski |
| 2011/0184487 A1 | 7/2011 | Alberts |
| 2011/0266977 A1 | 11/2011 | Tobey |
| 2012/0081337 A1 | 4/2012 | Camp |
| 2012/0116244 A1 | 5/2012 | McIntyre |
| 2012/0214143 A1 | 8/2012 | Severson |
| 2012/0330182 A1 | 12/2012 | Alberts |
| 2013/0022214 A1 | 1/2013 | Dickins |
| 2013/0135261 A1 | 5/2013 | Hardie-Bick |
| 2013/0310716 A1 | 11/2013 | Alberts |

FOREIGN PATENT DOCUMENTS

| | | |
|---|---|---|
| WO | WO2011017778 A1 | 2/2011 |
| WO | WO2012025733 A1 | 3/2012 |
| WO | WO2013011515 A1 | 1/2013 |
| WO | WO2013012739 A1 | 2/2013 |

* cited by examiner

TOUCH SENSITIVE SYSTEM AND METHOD FOR COGNITIVE AND BEHAVIORAL TESTING AND EVALUATION

CROSS-REFERENCE TO RELATED APPLICATIONS

This application claims under 35 U.S.C. §119(e) the benefit of U.S. Provisional Application 61/772,474 filed on Mar. 4, 2013, the content of which is incorporated in its entirety.

STATEMENT REGARDING FEDERALLY SPONSORED RESEARCH OR DEVELOPMENT

The present invention was developed in part with funds from the National Science Foundation Grant 0924636. The United States Government has certain rights to the invention.

TECHNICAL FIELD

This disclosure relates generally to the field of medical informatics. More specifically, the disclosure relates to the computerized determination, evaluation or testing of diagnostically relevant data, in particular, for assessing the normality of cognitive or executive function of the human brain.

BACKGROUND

Reaction times (RT), also called response times, and error rates (ER) on simple behavioral tasks have been shown to be valuable diagnostic tools for assessing the normality of cognitive or executive function of the human brain. Response time measures the amount of time it takes for a person to make a decision and effect a response following the presentation of a stimulus, and is a very common measure in experimental psychology to examine sensation, perception, cognitive, and motor function.

Cognitive dysfunction can arise with varying severity. Two commonly used clinical techniques are adequate to evaluate cognitive function in moderate to severe cases: brain imaging (functional magnetic resonance imaging, positron emission tomography, magnetoencephalography, or electroencephalography) and neuropsychological testing. Neuropsychological and imaging tests are generally not sensitive to detect subtle cognitive deficits. Neuroimaging methods are the least sensitive of all and are useful for predicting cognitive functional changes only if brain injury is moderate to severe. There are other problems beyond lack of sensitivity in neuropsychological and imaging techniques. The brain imaging technique is not portable, requires expertise to administer, and is slow to produce results. It is also very costly and is unsuitable for repeated use as would be needed for longitudinal monitoring. Neuropsychological testing also takes a relatively long time, requires expertise to administer and evaluate, and is very sensitive to language related issues. Some neuropsychological tests are unsuitable for repeated testing because of practice effects, learning, and strategies. These shortcomings negatively impact the ease of administration and interpretation and field applicability of these techniques.

Another clinical technique for measuring cognitive and executive functions in humans is eye movements. Eye movements have demonstrated brain areas important for processing visual stimuli and generating stimulus driven eye movement responses. Eye tracking devices track eye movements such as a saccade, which is a brain initiated quick simultaneous movement of both eyes in the same direction. Prosaccade eye movements involve a reflexive motor movement directly to a target. An antisaccade task is a voluntary eye movement task that involves inhibition of the reflexive movement towards the target and generation of a voluntary or goal directed movement of the eyes in the opposite direction of the target location[20-22] (the superscripts refer to publications listed by numerical sequence in the "Publications" part of written description immediately preceding the Claims). An antisaccade test can be used to determine deficits in executive functioning.[16-19] Several studies have demonstrated that eye tracking tasks are more sensitive than standard neuropsychological testing in detecting differences in cognitive or executive function[12-14]. For example, publication number 12 ((Hill S K, Reilly J L, Harris M S, Khine T, Sweeney J A (2008) *Oculomotor and neuropsychological effects of antipsychotic treatment for schizophrenia*. Schizophr Bull 34:494-506)) showed that eye tracking (or oculomotor) biomarkers were more sensitive to treatment-related changes in neurocognitive function than traditional neuropsychological measures.

Detecting mild cognitive dysfunction is extremely important because many of these mild problems if not detected early can lead to serious and sometimes fatal long-term outcomes. It is thought that less violent head impacts that are repeated in a short interval can be more damaging. This problem has reached national attention in the sport of professional football where subtle brain injuries have resulted in long term effects on memory and emotional functions and have raised awareness in a much greater population of people who participate in youth sports with potential for head impacts. Early detection of mild cognitive dysfunction is also very important for men and women in our armed forces as well as for emergency rooms throughout the country due to car or bicycle accidents and falls. Being able to track small changes in cognitive function will allow us to determine the most effective guidelines, interventions, and treatments. Cognitive deficits occur in many human brain disorders including psychiatric (e.g., schizophrenia), developmental {e.g., attention deficit hyperactivity disorder), and neurological {e.g., Huntington's disease). Detecting subtle differences in cognitive deficits is important for diagnosis or distinguishing subtypes that require different treatments or to identify the intervention, treatment or drug with optimal cognitive outcome. Thus early detection of mild cognitive dysfunction may also help with diagnosis, evaluation and discovery of treatments.

As mentioned, eye-tracking devices are able to detect subtle cognitive deficits with good temporal resolution for precise measurement of behavioral response times. Unfortunately, these devices are six figure expensive, time intensive, cumbersome, cause physical discomfort (wearing device(s) on the head, lengthy physical restraint of head requiring long motionless periods for accurate assessment), use elaborate and complicated machinery requiring complicated environmental control, require constant calibration and maintenance, necessitate training and expertise by someone with technical expertise to be accurate in administering the test, and require substantial data analysis.

There is therefore a great need for an inexpensive (thus potentially easily and widely available), portable and field operable, simple to operate device not needing constant calibration and maintenance for quick detection and monitoring of cognitive dysfunction, especially mild or subtle cognitive dysfunction, that can be used on school or professional sports sideline or locker room examinations, or in doctors offices or outpatient care, or in battlefield emergency care or other places in the field, or for low cost educational uses for health care professionals.

Recently, portable computing devices have become available that combine a display and a touch sensitive surface, allowing the user to interact with the display using touch with their own fingertips. However, in their current state, touch sensitive devices do not have touch temporal resolution sufficient to meet the need for in the field quick, accurate and precise detection and monitoring of cognitive dysfunction, especially mild or subtle cognitive dysfunction.

BRIEF SUMMARY OF THE INVENTION

Embodiments are disclosed that provide portable, field-convenient, potentially widely-available, simple to operate apparatus using methods and systems that are free of age and language constraints yet are highly sensitive for probing cognitive function. The embodiments include a touch sensitive device with special signal processing techniques that provide a temporal resolution comparable to expensive eye tracking data acquisition systems. The embodiments include or make use of one or more modules implemented at least partially in a set of instructions in software and configured to measure user reaction times to visual stimulus to a touch screen device having a capacitive sensor touch-sensitive surface and a detector of audio waves resulting from touch on the touch-sensitive surface. The modules employ recordation of acoustic vibrations resulting from a user's touching a target location on the touch screen surface spaced from a touched starting location on that surface to measure temporal response to a visual stimulus placed at the target location.

The embodiments provide a quick process (method) of assessing sensory-motor and executive function in a subject to measure and/or track sensory-motor and cognitive changes due to impact to the head, thereby to enable treatment or intervention. Tests can be completed on site at a speed of four to eight minutes in present embodiments. The utility of such a portable and user friendly diagnostic device in contexts such as youth or professional bodily impact sports or in combat zones or in emergency rooms or doctors offices, or for clinical neurophysiological determination and tracking of brain degeneration due to disease or ageing, and/or developmental changes, has implications for rapid and universally accessible screening and diagnostic tools for brain injuries.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION OF THE INVENTION

Figure 1:
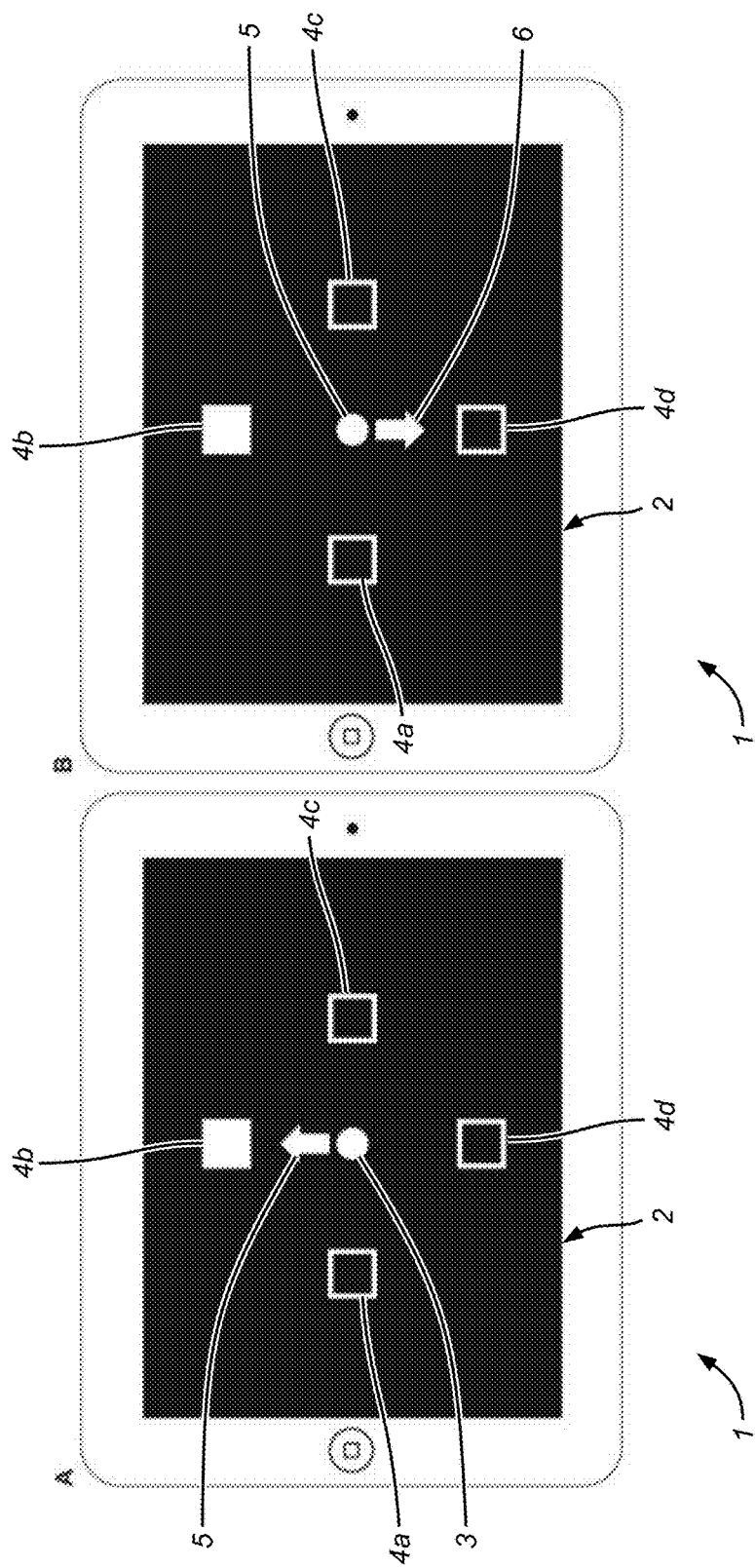
FIG. 1 is a schematic of an embodiment displaying two tasks on a touchscreen of a tablet computer for testing cognitive function in an embodiment of the invention.

General Preliminary Comments on Embodiments and Terminology

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure. Embodiments discussed herein can be implemented in suitable computer-executable instructions that may reside on a computer readable medium (e.g., a hard drive, flash drive), hardware circuitry or the like, or any combination.

The embodiments make use of a touch screen device having a touch-sensitive surface. The touchscreen device may be configured in a variety of ways. For example, the touchscreen device may be configured as part of a mobile communication device such as a mobile phone, a tablet computer, as part of a traditional computing device (e.g., a display device that is part of a laptop or personal computer), and so on. The touchscreen of the touchscreen device is configured to detect contact when being touched with a finger of a user's hand with the touchscreen using touch sensors. Examples of such touch sensors include capacitive touch sensors. In a projected capacitance an X-Y grid may be formed across the touchscreen using near optically transparent conductors (e.g., indium tin oxide) to detect contact at different X-Y locations on the touchscreen. Other capacitance techniques are also contemplated, such as surface capacitance, mutual capacitance, self-capacitance, and so on.

Generally, any of the functions described herein can be implemented using software, firmware, hardware (e.g., fixed logic circuitry), or a combination of these implementations. For example, the touchscreen device may be implemented using a computing device. The computing device may also include an entity (e.g., software) that causes hardware of the computing device to perform operations, e.g., processors, functional blocks, a "system-on-a-chip," and so on. The program code can be stored in one or more computer readable memory devices. The term "module" as used herein generally represents software, firmware, hardware, or a combination thereof.

At least portions of the functionalities or processes described herein can be implemented in suitable computer-executable instructions. The computer-executable instructions may be stored as software code components or modules on one or more computer readable media. In one embodiment, the computer-executable instructions may include lines of complied C++, Java, HTML, or any other programming or scripting code. In the case of a software implementation, the module represents program code that performs specified tasks when executed on a processor.

A "processor" (e.g., CPU or CPUs) includes any hardware system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc. Portions of processing can be performed at different times and at different locations, by different (or the same) processing systems.

The features of the techniques described below are platform-independent, meaning that the techniques may be implemented on a variety of commercial computing platforms having a variety of processors.

The computing device may include a computer-readable medium that may be configured to maintain instructions that cause the computing device, and more particularly hardware of the computing device to perform operations. Thus, the instructions function to configure the hardware to perform the operations and in this way result in transformation of the hardware to perform functions. The instructions may be provided by the computer-readable medium to the computing device through a variety of different configurations. A "computer-readable medium" may be any medium that can contain, store, communicate, propagate, or transport data or a program for use by or in connection with an instruction execution system, apparatus, system or device. The computer readable medium can be, by way of example, but not by limitation, an electronic, magnetic, optical, electromagnetic, infrared, or semiconductor system, apparatus, system, device, propagation medium, or computer memory. Such computer-readable medium shall generally be machine-readable and include software programming or code that can be human readable (e.g., source code) or machine-readable (e.g., object code). One such configuration of a computer-readable medium is a signal-bearing medium configured to transmit the instructions (e.g., as a carrier wave) to the hardware of the computing device, such as via a network. The computer-readable medium may also be configured as a computer-readable storage medium and thus is not a signal bearing medium. Examples of a computer-readable storage medium include a random-access memory (RAM), read-only memory (ROM), an optical disc, flash memory, hard disk memory, and other memory devices that may use magnetic, optical, and other techniques to store computer-executable instructions and other data executable by the CPU. But within this disclosure, the term "computer-readable medium" is not limited to ROM, RAM, and HD and can include any type of data storage medium that can be read by a processor.

An embodiment can include one or more computers network. In an embodiment, the computer has access to at least one database over the network.

Additionally, the functions of the disclosed embodiments may be implemented on one computer or shared/distributed among two or more computers communicatively coupled in, to or across a network. Communications between computers implementing embodiments can be accomplished using any electronic, optical, radio frequency signals, or other suitable methods and tools of communication in compliance with known network protocols.

Any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such nonlimiting examples and illustrations includes, but is not limited to: "for example," "for instance," "e.g.," "in an embodiment."

As used herein, the terms "comprises," "comprising," "includes," "including," "has," "having" or any other variation thereof, are intended to cover a non-exclusive inclusion. For example, a process, process, article, or apparatus that comprises a list of elements is not necessarily limited to only those elements but may include other elements not expressly listed or inherent to such process, process, article, or apparatus. Further, unless expressly stated to the contrary, "or" refers to an inclusive or and not to an exclusive or. That is, unless otherwise indicated, the term "or" is generally intended to mean "and/or". For example, a condition A or B is satisfied by any one of the following: A is true (or present) and B is false (or not present), A is false (or not present) and B is true (or present), and both A and B are true (or present).

As used herein, a term preceded by "a" or "an" (and "the" when antecedent basis is "a" or "an") includes both singular and plural of such term (unless in context the reference "a" or "an" clearly indicates only the singular or only the plural).

As used in the description herein, the meaning of "in" includes "in" and "on" unless the context clearly dictates otherwise.

Description of Embodiments

Our objective was to develop a variant of the well-established antisaccade task for testing frontal-lobe executive function but instead of using traditional eye tracking apparatus we wanted a device designed to be portable and field operable, potentially easily and widely accessible, free of language and age constraints, simple to use, but highly sensitive for probing cognitive functions.

To address the need for portability and field operability, we chose a touch sensitive tablet device for testing. The initial development was conducted on an Android™ operating system tablet having a touch screen interface. However, for better consistency with other lab hardware platforms, the final prototype of one embodiment was developed for an Apple iPad® touch screen tablet computer. (All references herein to an iPad tablet in development work, and in the field-testing in the Examples, are to the first generation iPad unless specific reference is made to the successor model "iPad2.")

We then addressed the need for very high sensitivity of probing cognitive functions using a touch screen portable tablet computer. Without highly sensitive tests, it would be impossible to measure mild cognitive changes (either deficits or enhancements, for example with interventions). We developed a simple iPad-based application based on a variant of the well-established antisaccade task for testing frontal-lobe executive function. We wanted the testing to be as simple as possible and administered with minimal language and age requirements. Point responses by the hand towards a target are similar to prosaccade eye movements in that they both involve a more reflexive motor movement directly to a target; while point responses away from a target are more similar to antisaccade movements as they also involve inhibition of the reflexive movement towards the target and generation of a voluntary or goal directed motor movement in the opposite direction of the target location[20-22]. Point responses by the hand towards a target herein are called "Pro-Point." Point responses away from a target herein are called "Anti-Point." We designed the application to implement complementary Pro-Point and Anti-Point tests.

Referring to FIG. 1, panel A shows a touch screen tablet device 1 with a touch sensitive surface 2 in which a first fixed location 3 is generated by the application (here, a central dot) and a plurality of additional fixed locations 4a, 4b, 4c, 4d are generated (here square frames) equally radially spaced from first location 3 on touch sensitive surface 2. At least one of the additional locations 4a, 4b, 4c, 4d is opposite another one of the additional locations 4a, 4b, 4c, 4d. For example, location 3b is location opposite 3d. All additional locations 4a, 4b, 4c, 4d are equally circumferentially spaced from a next circumferentially adjacent additional location. For example, location 4b is next circumferentially adjacent additional location 4a.

Panel A of FIG. 1 shows a Pro-Point task with a white arrow 5 (not part of the application) indicating a direction of a correct response, which is toward the target square 3b where a visual stimulus (white illumination) has been generated by the application.

Figure 2:
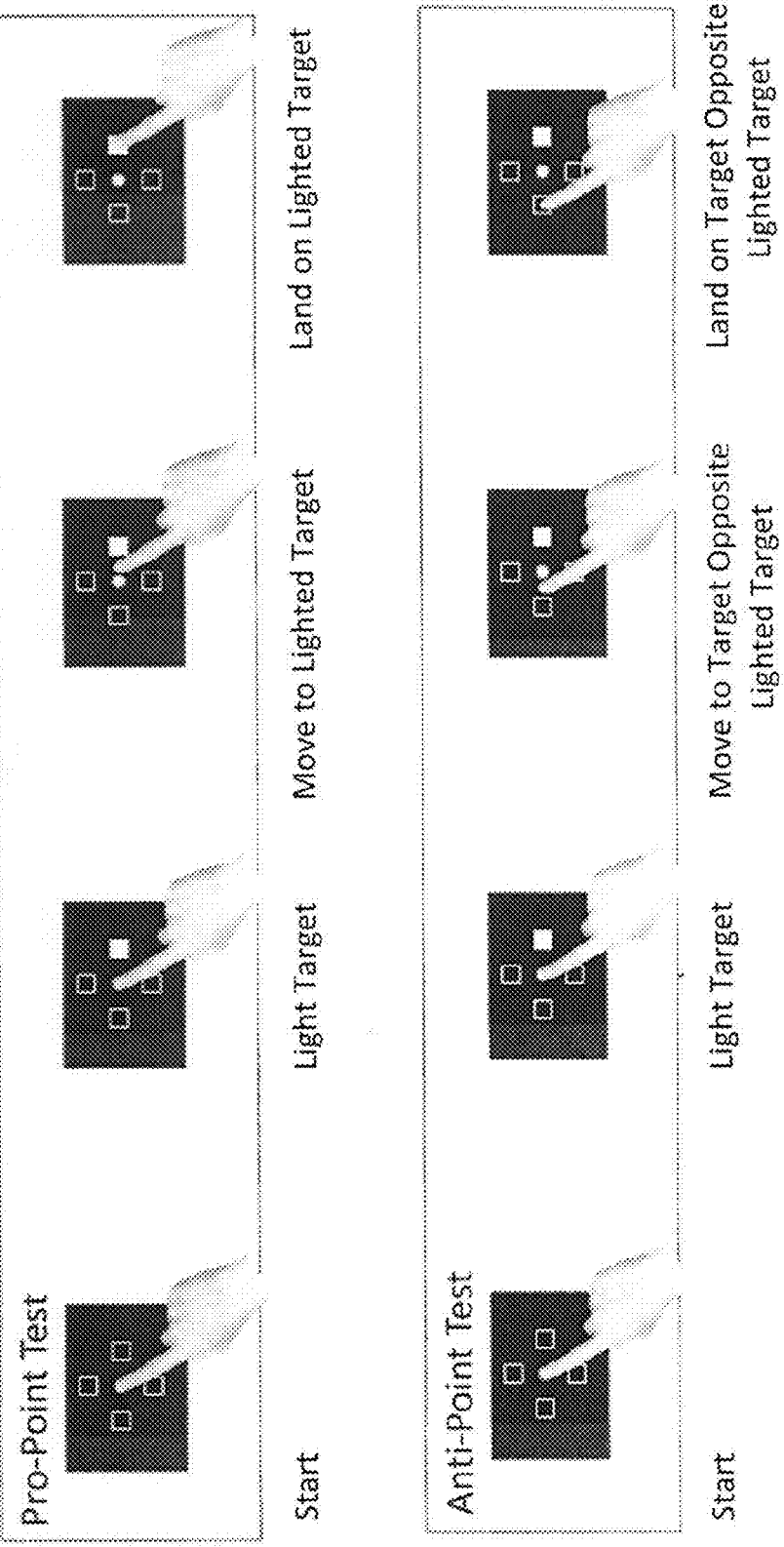
FIG. 2 is a schematic displaying finger touches on a touchscreen of an embodiment for a Pro-Point task and an Anti-Point Task for testing cognitive function.

Panel B of FIG. 2 shows an Anti-Point task with white arrow 6 indicating direction of a correct response (away from the target square 3b where a visual stimulus light has been generated).

The iPad touch screen generates capacitance signals on touching that are captured to record Pro-Point and Anti-Point touch responses.

Referring to FIG. 2, in the application we developed, at the beginning of a test trial the touch screen on a tablet computer displays a dot at the center of the screen and displays four white frames surrounding center dot (see FIG. 2, top). The test subject puts his/her finger on the central dot and holds it there. After a delay, a white square appears randomly in one of the four white frames surrounding the dot (white square location chosen randomly). The subject is instructed to touch the location at which the white square appears as soon as possible. The pro-point test consists of 48 trials administered in two blocks of 24 trials. A set of a minimum of 48 correct Pro-Point trials are rapidly repeated. If the wrong square is touched or if there is too long a delay is responding to the visual stimulus of the flashed white square, a trial error is recorded and added to the 48 correct trials. This is the Pro-Point test. It serves as a control for general alertness, sensorimotor function, and stimulus driven brain functions. Various trial specific items are recorded on each trial, including the time elapsed between the display of the white square and the exact location where the finger first landed.

The Anti-Point test (FIG. 1, bottom) is identical to the first test in all aspects except one: in this test, the subject is instructed to touch the location opposite to where the white square appeared as soon as possible. Additional time needed for the second task reflects additional cognitive processes (inhibition of stimulus driven responses and willful generation of a response). Further, any changes (with respect to an individual's baseline for repeated testing or with respect to another control population) that might only occur in the performance in the second test (but not the first test) can be attributed to changes in cognitive functions.

Figure 5A:
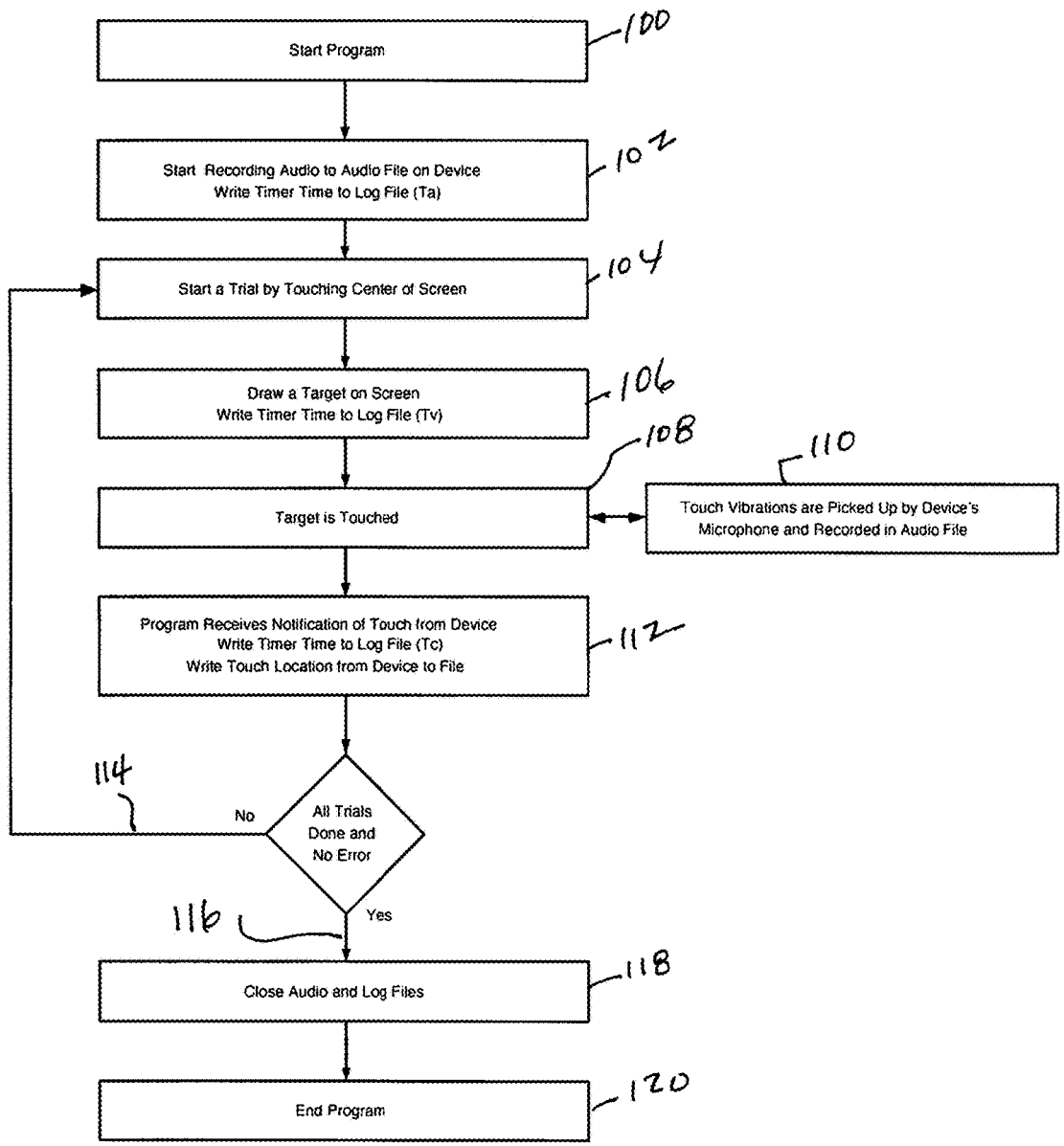
FIG. 5A is a block diagram of a method and system according to an embodiment of the invention for measuring and recording user touch task reaction times on a touchscreen device in a test for cognitive function.

The foregoing procedures are embodied in a set of instructions for a computing device as depicted in the block diagrams of FIG. 5A. Referring to 5A, data is collected. At 100, a program of instructions is started for a tablet computer 1 having a touch screen 2 (reference FIG. 1). At 102, the program directs the tablet computer 1 to start recording audio vibrations to an audio file in a computer readable medium of the touch screen device and to write timer time to a log file (Ta) on a computer readable medium. At 104 the user being tested starts a trial by touching the center (center 3 of FIG. 1) of the screen 2. At 106, the program directs the tablet computer 1 to draw (light) a target on one of the squares 4a, 4b, 4c or 4d of the touch screen 2 and write a timer time to a log file signifying the time the target is drawn (Tv). At 108, the user touches a target (either the drawn lighted square in a Pro-Point trial or a square opposite the lighted square in an Anti-Point trial). At 110 the computer microphone 7 picks up vibrations created by the user's touch of target and writes a timer time to a log file signifying the time the touch vibrations are sensed by microphone 7 (Tt). At 112, the computer receives notification of touch from the touch screen of the computer and the location coordinates of the touch and writes a timer time to a log file signifying the time the notification is received (Tc) and write the location of touch to file. A set of a number of error free trials (48 in the examples described herein) is conducted at 114 by instruction to return to 104 and start another trial, until the full set is completed, as at 116, at which time, at 118, the computer is instructed to close the audio and log files onto a computer readable medium which may be in the computer or in communication with the computer, whereupon at 120, the program of instructions is ended.

The foregoing comprises a system and method of measuring user reaction times to visual stimulus on a portable touch screen device having a capacitive touch-sensitive surface, an acoustic sensor proximal the surface, and one or more modules implemented partially in software, the modules being responsive to a user start command to a) open a time log file on receipt of the start command; b) coincident with step a), commence recording for input signals from the acoustic sensor to an audio file and write a timer time to a log file signifying the time of the start of this monitoring (Ta); c) generate a visual stimulus at a first location on the touch screen surface for touch by a user; d) generate at least one second visual stimulus at a second location on the touch screen surface spaced from the first location and write time of generation of the second visual stimulus to a log file signifying such time of generation (Tv); e) receive notification of capacitance sensed touch and coordinates of such sensed touch and write timer time to a log file (Tc) signifying time of such sensed touch and also write the sensed touch coordinates location to a file; f) remove the second visual stimulus from the touch screen surface, steps c)-f) comprising a single trial; and g) repeat steps c)-f) until a set of trials signified by a predetermined number of capacitance sensed touches (Tc) of the second location attains a preset number, then cease repeating steps c)-f), and close the audio and log files onto a computer readable medium which may be in the computer or in communication with the computer.

The Pro-Point and Anti-Point embodiments of the foregoing system and method are ones in which step b) further comprises generating a first fixed location and a plurality of additional fixed second locations equally radially spaced from the first location on the touch sensitive surface, at least one such additional second location being opposite another such additional location and any additional second locations being equally circumferentially spaced from a next circumferentially adjacent additional second location, and step d) further comprises generating at least one second visual stimulus on one of the additional second locations on the touch sensitive surface.

Correctness of timing of the recordation of events in our measurement system comprising a developed Pro-Point and Anti-Point test using a touchscreen device is critical to detection of mild or subtle cognitive impairment. Essentially our measurement system is a timing device. It measures time of response to visual stimulus. The purpose of the system is to get timing values that are as close as the system permits to true or real world values and to do this repeatedly. The accuracy of a measurement system is the degree of closeness of measurements of a quantity to that quantity's actual (true) value. The precision of a measurement system, related to reproducibility and repeatability, is the degree to which repeated measurements under unchanged conditions show the same results. Correctness requires accuracy and precision.

It is well known that touchscreen devices are slow to detect that they are being touched. Modern touchscreen devices internally use a capacitive touch sensitive mechanism that does not have the high temporal resolution necessary for precise measurement of behavioral response time. Typically, current capacitive touch-based devices are polled at 60 Hz and are able to report a change in touch status (e.g. contact) every 50 or so milliseconds, even when screen refresh rates and processors are super fast and optimal.

In order to examine the correctness of timing of various events in the system (e.g. when the visual stimulus at a square 4a, 4b, 4c, or 4d is turned on and when the finger touches a designated location in reaction to that stimulus), we examined the timing externally, i.e., independently of the iPad's internal capacitance touch signaling system and recording system. Referring to FIG. 2 the test subject is shown touching the center dot. A light trigger in a covered corner location of the tablet device was programmed to flash the exact time a target was presented on a stimulus square. A photodiode aligned with the location of the light trigger reacted to the light trigger and generated a pulse captured and recorded by an oscilloscope to capture the exact time the stimulus appeared on the screen. Still referring to FIG. 2, the subject lifts off the center spot and touches the square opposite the presented target. In order to determine if the finger's landing time is registered precisely, a piezo acoustic transducer sensor was used. A piezo acoustic transducer sensor detects vibrations. The moment that the finger lands on the iPad again, the piezo sensor produces an electrical signal that is captured by oscilloscope 32 and recorded. Conventional analog to digital processing circuitry was employed to convert analog electrical signals to digital signals that were recorded.

A 5 mW red laser module can be used to illuminate a photodiode placed on the opposite side of an iPad. The photodiode detects light coming from a laser. Referring to FIG. 2, as long as the finger is still touching the iPad, light from laser does not reach the photodiode. One can measure the moment a finger is lifted to move to a target, because laser light reaches laser light receiving photodiode and the exact time of the electrical signal arising from photodiode can be captured and recorded. This test can be used to calibrate use of a detection of audio vibrations caused when a finger is lifted from the center spot as a signal for start of the timing of movement from center spot to a presented target or opposite a presented target.

This external capture of the time elapsed between onset of visual target and when touch is sensed was compared to the time elapsed between onset of visual target ("Tv", as further explained below) and when touch is sensed and internally registered on the iPad itself ("Tc", as further explained below). We found that the elapsed time for when the target was detected touched by the native iPad capacitance scheme (iPad latencies) was significantly slower than when touch was recognized by external means (real-world touch latencies). We also did additional control tests to verify that the slower times were not due to a delay in the internal registration of the visual onset but specifically in the internal recognition and registration of touch. The native touch screen events did not provide the temporal resolution necessary for achieving the high sensitivity needed for validity of the two Pro-Point and Anti-Point tests. More particularly, using the laser detection system described above for stimulus onset and piezo transducer for sensing touch, we found that the error in iPad capacitive-based touch latencies (i.e., time between stimulus onset and capacitive touch latency) compared to the recorded real-world touch latencies was 63.59 ms greater than the recorded real-world touch latency and on average had a calculation variance of 44. (As used herein, "ms" means millisecond or "msec" and the terms "ms" and "msec" are used interchangeably). Using the light trigger/photodetector system described above for stimulus onset and piezo transducer for sensing touch on an iPad2, we found that the recorded real-world touch latencies was 72.24 ms greater the recorded real-world touch latency and on average had a calculation variance of 35 Thus we were faced with two problems. The main problem was lack of accuracy using the iPad (capacitive-based) touch latencies and the secondary problem was lack of precision.

Figure 3:
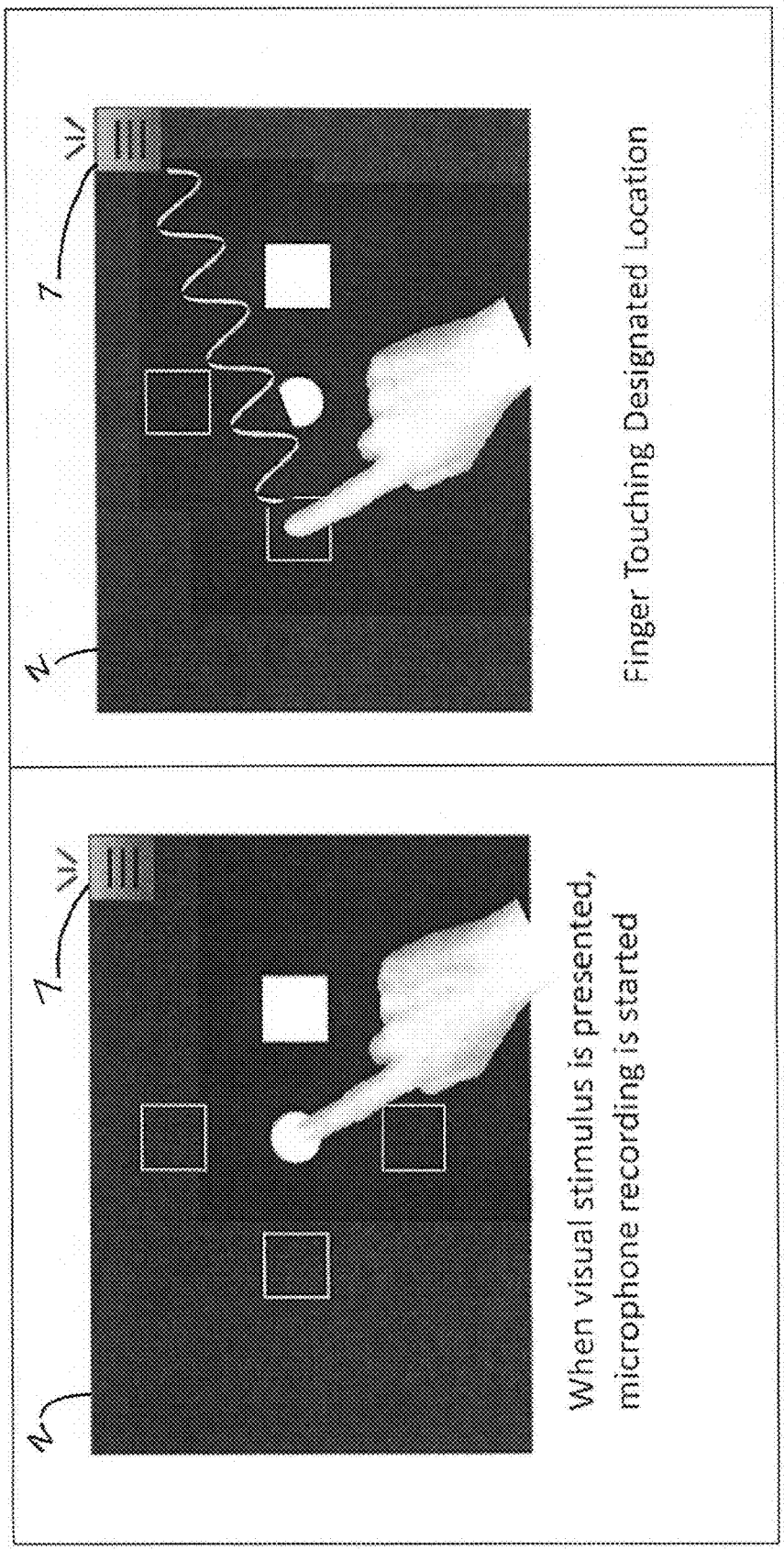
FIG. 3 is a schematic displaying finger touches on a touchscreen device of an embodiment for an Anti-Point Task for testing cognitive function, wherein touch of the target destination creates acoustical vibrations that are sensed by an internal microphone of the device.

For the main problem in using the iPad touchscreen for cognitive testing (lack of touch detection precision because iPad's native mechanism for sensing touch is capacitance based), a mechanism had to be designed to provide significantly enhanced temporal resolution (variability reduction from about 44 or 35 msec to sub millisecond). To improve precision of the touch, in one embodiment we used the built in microphone on the iPad to add information from a recorded audio trace of the touch with a sampling rate 44 kHz (sampled every 0.02 ms). In an embodiment, referring to FIG. 3, an internal microphone 7 of the tablet device starts recording when the visual stimulus at one of the four squares 4a, 4b, 4c or 4d is presented. The tablet device records the time ("Tv") the visual stimulus is presented to a target 4a, 4b, 4c or 4d. Microphone 7 records the sound vibrations caused when a target square is touched ("Tt"). In FIG. 3, the test is Anti-Point, and the target square 4a opposite presented target square 4c is touched. However, given there was a large unknown delay from the time when a command to start audio recording is sent to the iPad and the time when a first audio sample is acquired, it was not clear how to align the capacitive touch timer with the audio timer.

In order to utilize the information in the audio recording to reduce the large variance in the touch (capacitance) latency, we estimated the variability in the touch latency using the audio trace and then removed it from the capacitive touch latency. In order to solve the problem of the audio recording's initial delay, we opened the audio recording only once before the task begins Second, we calculated the average difference between the two timers (i.e., the average difference between the time of the audio signature of touch and the time of the touch from the capacitive touch timer) across a set of trials. Third, we adjusted the touch (capacitance-based) latency on a given trial by adding the variability of the audio signal on that given trial (i.e., add the time of the audio signature of touch on that specific trial minus the average time of the audio signal calculated in the second step). In this way, we were able to reduce the variance of the error in estimating the touch latency from, in this case, 44 ms (touch capacitance signal alone) to 0.2 ms (combined touch capacitance and trial specific audio variability estimated using the audio trace). Thus with this processing, our test system had a temporal resolution for touch of about 0.2 msec. To reject other noise that may be picked up during the trial, the system looked for the distinct signatures in the vicinity of the time reported by the iPad's native touch mechanism.

For the secondary problem (lack of accuracy of the iPad reported touch latency), the accuracy of the iPad reported touch latency is improved by subtracting the device delay constant from the capacitive-based latency. This improves the accuracy of the average estimate of latency, but the precision will remain variable (variance 44 ms). This device delay constant appears to be consistent and constant for a given hardware, software, and operating system and can be determined in several ways with tools currently available using an external device as described above where we describe the observations that let to the solutions we describe.

The primary and secondary corrections of the captured data for accuracy and precision described above is mathematically explained below in reference to FIG. 4.

Nomenclature

Figure 4:
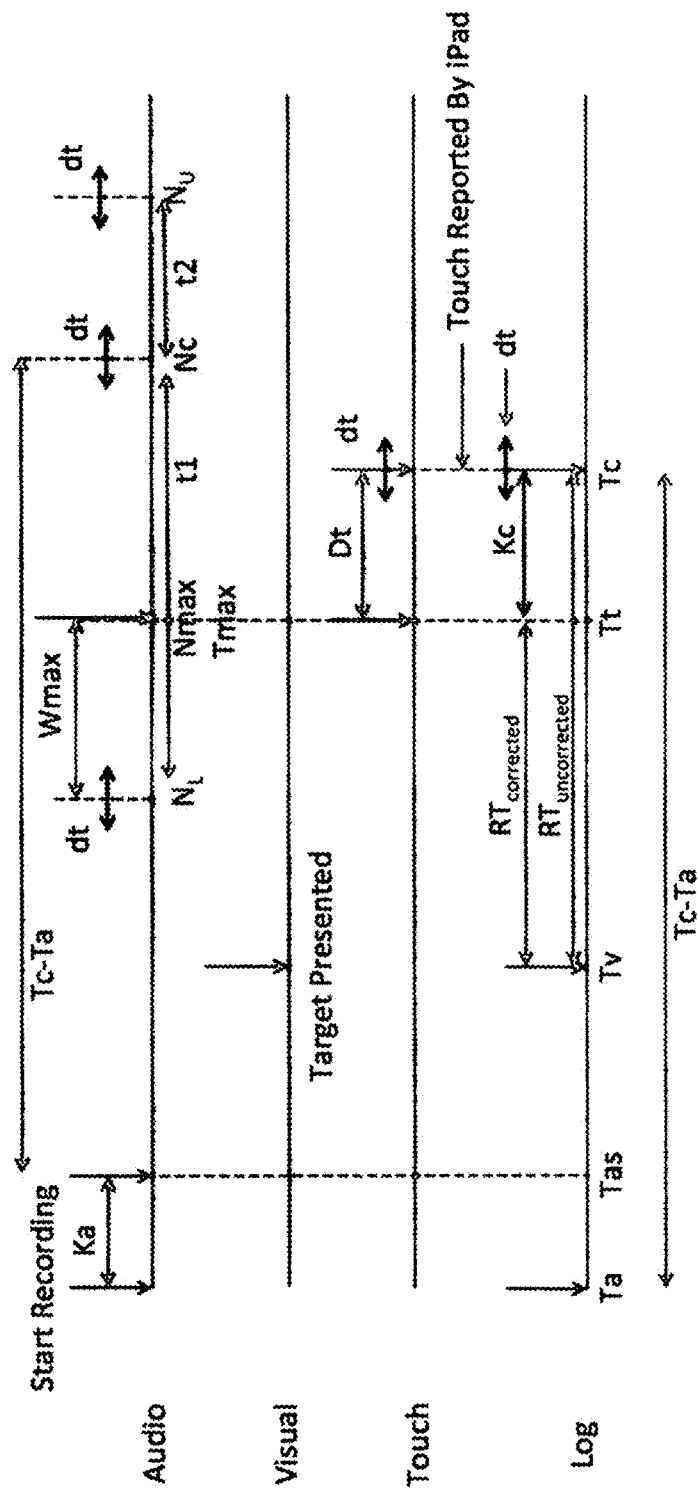
FIG. 4 is a chart of audio, visual and touch event and log timer times of the events in the methods and systems of FIGS. 5A and 5B.

The abbreviations on the chart in FIG. 4 have the following meanings:

Ta Time at which command to start audio recording is sent to iPad, time also recorded in .log file.
Tas Time at which first audio sample is acquired.
Ka Constant within a test session, representing the delay between time recorded in .log file (Ta) and the time when first sample is collected in audio file (Tas) in msec.
Tv Time at which command to draw Target stimulus is sent to iPad, time also recorded in .log file.
Tt Time at which the touch actually occurred.
Tc Time at which iPad sends the event that a touch has occurred, time also recorded in .log file.
Dt Variable delay between touch time recorded in .log file (Tc) and the time when the touch actually occurred (Tt) in msec.
  Dt=Kc+dt, where Kc is the Mean(Dt) and represents a constant offset that that will be used to improve accuracy; and where dt represents the trial-to-trial variation of the capacitive touch measure that will be used to improve precision.
  *Note: dt variation is carried through the system. (1) It determines the variation of Nc (see below). (2) It determines the variation of the lower and upper bounds, $N_L$ and Nu (see below). (3) Thus, it is the variation of Wmax (see Equation 5).
Kc: Is constant for a particular device and software configuration.
dt: Will be determined by a correction obtained from the audio recording.
Nc sample in audio file corresponding to a time delay of Tc−Ta from the first audio sample.
NL sample in audio file corresponding to an audio window lower bound, indexed from the first audio sample (Nc−t1).
Nu sample in audio file corresponding to an audio window upper bound, indexed from the first audio sample (Nc+t2).
Nmax peak sample in the audio file corresponding to the touch.
Tmax Time corresponding to the peak sample.
Wmax Time difference between NL and Nmax in msec.
Mean Wmax Average time difference between NL and Nmax across a set of trials.

Mathematical Treatments

In order to measure the Mean Dt (or Kc) for a particular device, the following procedure is used:
(1) Measure RT (response time) with iPad (internal measure) and also externally several times.
(2) Conduct a regression between the two measurements. external=iPad*slope+offset. (The external is the gold standard and it measures the true RTcorrected).
Therefore
RTcorrected=(Tc−Tv)*slope+offset=(RTcorrected+Dt)*slope+offset=>Dt=[RTcorrected*(1−slope)−offset]/slope. If slope~1, then Dt=−offset.
Therefore, the offset estimated with the above regression with a constraint of unit slope is the Mean Dt (or Kc).

In an iPad experiment without audio or external measurements, only Tc and Tv are available to estimate RT. Thus, as a first approximation:

$$\text{RTuncorrected} = Tc - Tv \quad \text{(Equation 1)}$$

To improve the accuracy and precision of RT on each trial, we need to subtract Dt from the above expression. Therefore:

$$\text{RTcorrected} = (Tc - Tv) - Dt \quad \text{(Equation 2)}$$

Dt varies from trial to trial with Mean(Dt) and Var(Dt) statistics. Therefore $$\text{RTcorrected} = (Tc - Tv) - (\text{Mean}(Dt) + dt) \quad \text{(Equation 3)}$$

where dt is the deviation from the mean on a given trial Mean(Dt) was externally measured, see above. So without audio, subtracting Mean(Dt) improves accuracy of RT but does not improve the precision of the trial RT. Thus, as a first approximation that corrects for accuracy only (without audio), $$\text{RTpartially\_corrected} = (Tc - Tv) - \text{Mean}(Dt) \quad \text{(Equation 3b)}$$

To improve precision of RT on each trial, dt on each trial has to be estimated. There is no way to estimate dt for each trial from the information gathered in either previous external measurements or in an iPad experiment without audio. In an iPad experiment with audio, Tc, Tv and audio samples (44 kHz sampling rate) whose collection was delayed by Ka are available. Ka is a constant delay for a particular experiment (since the audio recording is opened only once at the beginning of the experiment). Given the high sampling rate and precise audio signature of touch, it is assumes that any variability in the audio signature of touch is due to (equal and opposite to) the variability in the precision of the capacitive touch, dt. Hence:

$$dt=Dt-\text{Mean}(Dt)=\text{Mean}(W\text{max})-W\text{max} \quad \text{(Equation 4)}$$

[Terms are reversed because when Dt is bigger than the Mean(Dt), Wmax will be smaller than the Mean(Wmax). This is because the lower bound is variable and dependent on Dt. Thus, Dt values greater than the mean will result in Wmax values less than the mean. See the windowing procedure below.]

Therefore, Equation 3 becomes:

$$RT\text{corrected}=(Tc-Tv)-(\text{Mean}(Dt)+(\text{Mean}(W\text{max})-W\text{max})).$$

And simplified:

$$RT\text{corrected}=Tc-Tv-\text{Mean}(Dt)+(W\text{max}-\text{Mean}(W\text{max})) \quad \text{(Equation 5)}$$

Thus for equation 5 one must first find Wmax for each trial. To do this the following windowing procedure is used.

(1) Define a window in the audio file to search for the audio signature of touch, anchored around the sample in the file (Nc) corresponding to Tc−Ta msec from the first audio sample.
  (a) Window lower bound (NL): sample corresponding to Tc−Ta−t1 msec, indexed from the first sample.
  (b) Window upper bound (Nu): sample in the file corresponding to Tc−Ta+t2 msec, indexed from the first sample.
(2) Find the sample corresponding to the peak amplitude (audio signature of touch) within the window (Nmax).
  (a) Wmax is the time corresponding to the sample from Window start where the peak (audio signature of touch) occurs (Nmax).
  (b) Wmax=Tmax−(Tc−Ta−t1), where (Tc−Ta−t1) represents the time of the window lower bound, NL To calculate Mean(Wmax), for all trials in the experiment, find Wmax and average it. For each trial, estimate the corrected RT using Equation 5.

Figure 5B:
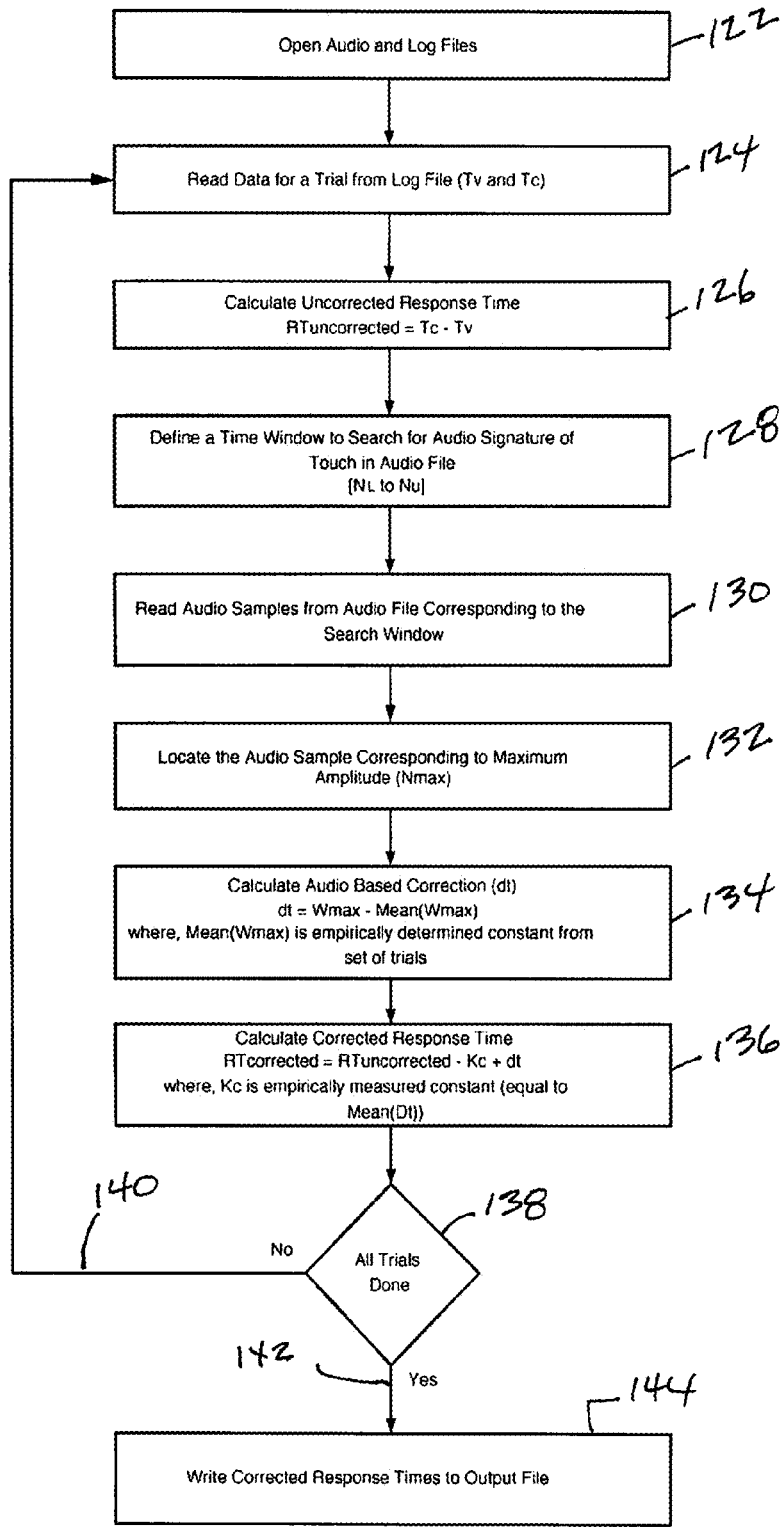
FIG. 5B is a block diagram of a method and system according to an embodiment of the invention for using data collected according to the method and system of FIG. 5A and correcting the data recorded by the touch screen device obtain accurate and precise reaction times in a test for cognitive function.

The foregoing is explained in reference to process at FIG. 5B. Referring to FIG. 5B, the data from the process of FIG. 5A is analyzed. A program of instructions is started for tablet computer 1 or a computer to which the data collected in the process of FIG. 5A is transmitted, and at 122 the audio and log files written in the process of FIG. 5A are opened. The program instructs the computer at 124 to read the Tv and Tc data for a trial from the log file; at 126, to calculate Tc−Tv (RTuncorrected); at 128 to define a time window bound (lower bound (NL) to an upper bound (NU)) to search for audio signature of touch in the audio file; at 130 to read audio samples from the audio file corresponding to the search window from NL to NU; at 132 to locate the audio sample corresponding to maximum amplitude (Mmax); at 134 to calculate audio based correction dt=Wmax−Mean (Wmax) where Mean(Wmax) is an empirically determined constant from a set of trials; at 136 to calculate corrected response time where RTcorrected=RTuncorrected−Kc+dt, where Kc is an empirically measured constant equal to Mean(Dt); at 138 whether all trials conducted in a set from FIG. 5A are completed is determined, if not, the set is completed by instruction to return at 140 to step 124 to read Tv and Tc data from another trial in the set and re-perform steps 126-138, until all trials are done, as at 142, at which time, at 144, the computer is instructed to write the corrected response times for the trials to an output. An output could be one or more of a computer file on the device, a summary file written on the screen of the touch screen device, a file shipped across the network to another computer or storage device, a file written to a USB device, a file sent to a print device or another means of capturing the information.

Thus an embodiment of method and system to determine user reaction time by correct Tc measured on a portable touch screen device having a capacitive touch-sensitive surface, an acoustic sensor proximal the one or more modules implemented partially in software, includes, in a computing device, which may be the same as the portable device or another computing device having one or more modules implemented at least partially in software and to which the data from the portable device is transmitted, comprises 1) opening the audio and log files from step g), 2) reading the data from the log file corresponding to Tv and Tc for each trial, 3) calculating uncorrected response time: RTuncorrected=Tc−Tv for each trial, 4) defining a time window to search for audio signatures of touch in the audio file for each trial, 5) reading audio samples from the audio file corresponding to the search window, 6) locating audio samples corresponding to maximum amplitude (Nmax), 7) calculating an audio based correction of dt=Wmax−Mean (Wmax), where Mean(Wmax) is an empirically determined constant from a set of trials comprising steps a)-f), 8) calculating a corrected response time RTcorrected=RTuncorrected−Kc+dt, where Kc is an empirically measured constant equal to Mean(Dt), and 9) writing the corrected response time to an output. As mentioned above, an output could be one or more of a computer file on the device, a summary file written on the screen of the touch screen device, a file shipped across the network to another computer or storage device, a file written to a USB device, a file sent to a print device or another means of capturing the information.

In an embodiment in which accuracy but not precision of a response time is adequate information, a method and system measures user reaction times to visual stimulus on a portable touch screen device having a capacitive touch-sensitive surface with a touch reporting mechanism, and one or more modules at least partially implemented in software, the modules being responsive to a user start command to a) open a time log file on receipt of the start command; b) generate a visual stimulus at a first location on the touch screen surface for touch by a user; c) generate a second visual stimulus at a second location on the touch screen surface spaced from the first location and write time of generation of the second visual stimulus to a log file signifying such time of generation (Tv); d) receive notification of capacitance sensed touch and coordinates of such sensed touch and write timer time to a log file (Tc) signifying time of such sensed touch and also write the sensed touch coordinates location to a file; e) remove the second visual stimulus from the touch screen surface, steps b)-f) comprising a single trial; e) repeat steps b)-e) until a set of trials signified by a predetermined number of capacitance sensed touches (Tc) of the second location attains a preset number, then cease repeating steps b)-e), and close the log file onto a computer readable medium which may be in the device or in communication with the device; and g) in a computing device, which may be the same as the portable device or another computing device having one or more modules implemented at least partially in software and to which the data from the portable device is transmitted, determine the user reaction time (RT) by 1) opening the log files from step f), 2) reading the data from the log file corresponding to Tc for each trial, 3) calculating uncorrected response time: RTuncorrected=Tc−Tv for each trial, 4) calculating response time corrected for accuracy: RTaccuracy corrected=RTuncorrected−Kc, where Kc is an empirically measured constant corresponding to the average latency of the capacitive touch reporting mechanism, and 5) writing the accuracy corrected response time to an output.

In one embodiment involving a portable touch screen device having a capacitive touch-sensitive surface and an acoustic sensor proximal the surface, time of touch of a second visual stimulus located separately from the first location of visual stimulus generated on the touch screen is not determined by system registration of capacitance and recordation of touch on the second location (Tc) but instead time of touch is determined from audio vibrations that occur on touch of the second location. This is essentially the system shown in FIG. 5A without use of Tc, which either can be eliminated or ignored.

This process using only audio vibrations that occur on touch of the second location to signify time of touch of the second location (Tt) (determined by the external measurements described above to be less than 2 msec from actual or true time of touch) is a process of measuring user reaction times to visual stimulus on a portable touch screen device having a capacitive touch-sensitive surface with a touch reporting mechanism, an acoustic sensor proximal the surface, and one or more modules implemented partially in software, the modules being responsive to a user start command to: a) open a time log file on receipt of the start command; b) generate a visual stimulus at a first location on the touch screen surface for touch by a user, c) coincident with step b), commence monitoring for input signals from the acoustic sensor and write a timer time to a log file signifying the time start of this monitoring (Ta); d) generate at least one second visual stimulus at a second location on the touch screen surface spaced from the first location and write time of generation of the second visual stimulus to a log file signifying such time of generation (Tv); e) record acoustical vibrations originating from user touch on the touch-sensitive surface at or near the second location as sensed by the audio sensor and write a timer time to a log file signifying initial recording of the sensed vibrations (Tt) originating from the second location and also write coordinates of the sensed touch location to a file; f) remove the second visual stimulus from the touch screen surface and stop monitoring the acoustical sensor, steps a)-f) comprising a single trial; g) repeat steps b)-f) until a set of trials signified by a predetermined number of auditory sensor sensed touches (Tt) of the second location attains a preset number, then cease repeating steps b)-f), and close the audio and log files onto a computer readable medium which may be in the computer or in communication with the computer; and h) in a computing device, which may be the same as the portable device or another computing device having one or more modules implemented at least partially in software and to which the data from the portable device is transmitted, determine the user reaction time (RT) by 1) opening the log files from step g), 2) reading the data from the log file corresponding to Tv and Tt for each trial, 3) calculating uncorrected response time: RT=Tt−Tv for each trial, and 4) calculating response time corrected for accuracy: RTaccuracy corrected=RTuncorrected−Kc, where Kc is an empirically measured constant equal to Mean(Dt), and 5) writing the accuracy corrected response time to an output, which could be one or more of a computer file on the device, a summary file written on the screen of the touch screen device, a file shipped across the network to another computer or storage device, a file written to a USB device, a file sent to a print device or another means of capturing the information.

Figure 6:
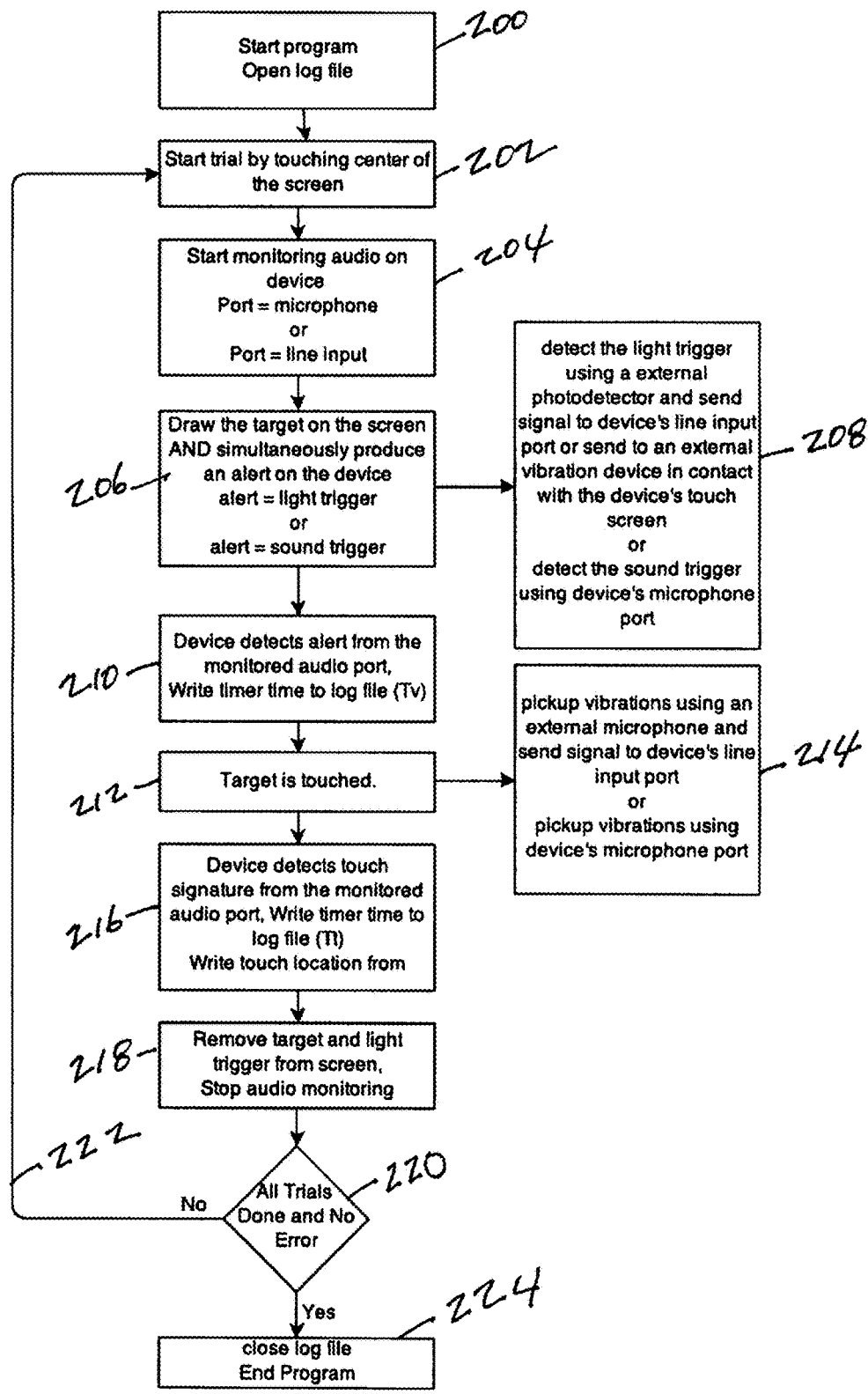
FIG. 6 is a block diagram of a method and system according to an embodiment of the invention for measuring and recording user touch task reaction times on a touchscreen device in a test for cognitive function for recording actual reaction times using a device created sound.

In another embodiment, instead of employing the touch screen device to write the time of presentation of a visual stimulus to a first location on the screen, an alert is generated at the time of presentation of a visual stimulus to a second location on the screen. The generated alert is detected, input to the device, and the time of such input is written to a timer log as Tv. All other functions of the foregoing embodiment that does not make use of Tc are employed. Referring to FIG. 6, a system and method in which an alert created by the device is detected by an external sensor, reported to the device, and the event is written to the timer log as Tv is shown. Referring to FIG. 6, on a portable touch screen device having a capacitive touch-sensitive surface with a touch reporting mechanism, an acoustic sensor proximal such surface, an alert signal generator, an alert signal detector, an audio input port, and one or more modules at least partially implemented in software, the modules respond to a user start command, at 200 to start the program and open a log file, at 202 to start a trial by touching a first location (center) of the touch screen, at 204 to start monitoring audio from the audio port either an internal microphone port or a line input on the device, at 206, to draw the target on the screen and simultaneously produce an alert on the device, such as by playing a brief sound buffer on an internal speaker of the device (a sound trigger) or generating a light on the screen such as by generating bright lighted pixels on the screen (a light trigger). At 208, the device detects the light trigger using an external photodetector and sends a single to the device's line input port or alternatively to an external vibration device in contact with the device's touch screen, or if a sound trigger is used, the device detects the sound trigger from the internal microphone, at 210 the device detects the alert from the monitored audio port and writes a timer time to the log file (Tv) signifying the presentation of the visual stimulus at the drawn target. At 212, the user touches a target (e.g., either the drawn lighted square in a Pro-Point trial or a square opposite the lighted square in an Anti-Point trial). At 214 vibrations created by the user's touch of the target are picked up by the computer's internal microphone port 7 or by using an external microphone that sends a signal to the device's line input port. At 216 the device detects the touch signatures from the monitored audio port, writes a timer time to a log file signifying the time of touch (Tt), and writes the location coordinates of touch to file. At 218 the device is instructed to remove the target, and if a light trigger is used, also the light trigger, from the screen and stop audio monitoring. At 220, a determination is made whether a set of a number of error free trials (48 in the examples described herein) is completed, and if so, as at 224 after "yes," the log file is closed onto a computer readable medium which may be in the device or in communication with the device, and the program of instructions is ended, but if a set of a number of trials is not completed, as at "no", the process repeats at 222 to start another trial at 202, and the entire process repeats until the full set is completed, as at 220 "yes," at which time, at 224, the log file is closed onto a computer readable medium which may be in the device or in communication with the device, and the program of instructions is ended.

In either the sound trigger embodiment or the light trigger embodiment, reaction time of the user is determined by opening the log files from 224, reading the data from the log file corresponding to Tv and Tt for each trial, calculating uncorrected response time: RT=Tt−Tv for each trial, and writing the response time to an output.

The process of either the sound trigger embodiment or the light trigger embodiment is more succinctly stated as a method of measuring user reaction times to visual stimulus on a portable touch screen device having a capacitive touch-sensitive surface with a touch reporting mechanism, an acoustic sensor proximal the surface, an alert signal generator, an alert signal detector, an audio input port, and one or more modules at least partially implemented in software, the modules being responsive to a user start command to a) open a time log file on receipt of the start command; b) coincident with step a), commence monitoring on the audio input port for input from the alert signal detector and write a timer time to a log file signifying the time of start of this monitoring (Ta); c) generate a visual stimulus at a first location on the touch screen surface for touch by a user; d) generate a second visual stimulus at a second location on the touch screen surface spaced from the first location and at the same time activate the alert signal generator and write time of receipt of a signal from the alert signal detector to a log file signifying the time of generation of the second visual stimulus (Tv); e) detect acoustical vibrations originating from user touch on the touch-sensitive surface at or near the second location as sensed by the acoustic sensor and write a timer time to a log file signifying initial recording of the sensed vibrations (Tt) originating from the second location and also write coordinates of the sensed touch location to a file; f) remove the second visual stimulus from the touch screen surface and stop monitoring the audio input port, steps b)-f) comprising a single trial; g) repeat steps b)-f) until a set of trials signified by a predetermined number of auditory sensor sensed touches (Tt) of the second location attains a preset number, then cease repeating steps b)-f), and close the log file onto a computer readable medium which may be in the device or in communication with the device; h) in a computing device, which may be the same as the portable device or another computing device having one or more modules implemented at least partially in software and to which the data from the portable device is transmitted, determining the user reaction time by 1) opening the log files from step g), 2) reading the data from the log file corresponding to Tv and Tt for each trial, 3) calculating response time: RT=Tt−Tv for each trial, and d) writing the response time to an output.

Figure 7:
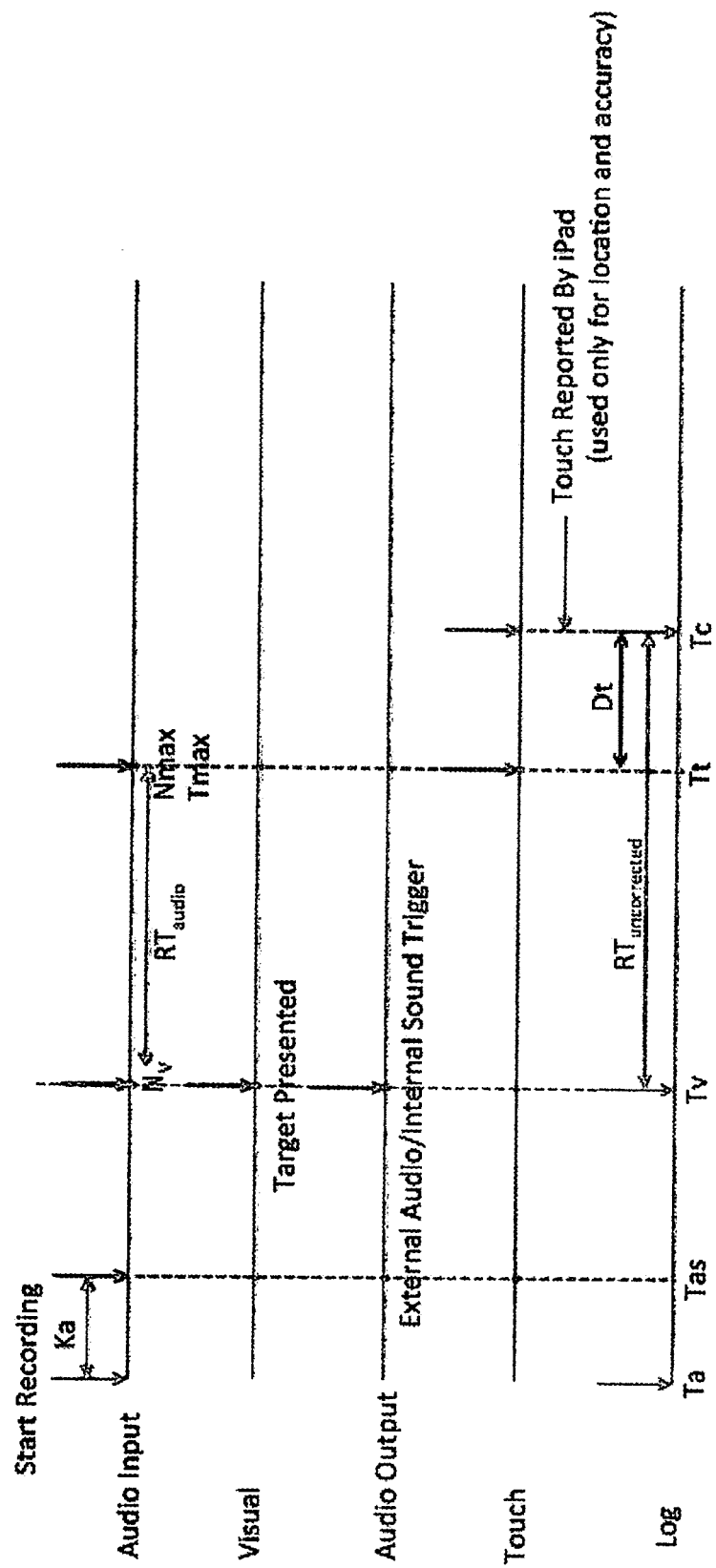
FIG. 7 is a chart of audio, visual and touch event and log timer times of the events in the methods and systems of FIG. 6.

FIG. 7 is a chart of audio, visual and touch event and log timer times of the events in the methods and systems of FIG. 6 and draws on the nomenclature set forth above.

Summarizing, we developed a method and system using a tablet based portable system with special signaling techniques precise enough for testing to detect mild cognitive changes (deficits/improvements). An individual self-administers two tests on a tablet device (e.g. an Apple iPad). In one test (the Pro-Point test), the individual responds to a visual stimulus on the tablet's screen by lifting his/her finger from a fixed center location and touching the location where the stimulus appeared as soon as possible. In the second test (the Anti-Point test), the individual responds to a visual stimulus on the tablet's screen by lifting his/her finger from a fixed center location and touching the location opposite to where the stimulus appeared. In both tests, the time the visual stimulus is presented and the time it takes to touch the appropriate location are recorded. In one embodiment, the times are recorded from the touch screen as well as the tablet's microphone system. Temporal accuracy and precision of pointing are corrected from these recorded coordinates. Also recorded are the coordinates of the location that was touched. In other embodiments, time of touch does not use the touch screens recognition and recording of time of touch, although the coordinates of the location that was touched as sensed by the touch screen are recorded. The time and spatial recordings are calibrated and reported with high temporal precision and spatial precision. The calculations and analysis can be performed by a program run in the tablet computer or the recorded data can be transmitted to a separate computer for that purpose and for storage and further analysis as desired. Everything that is needed to test an individual and analyze the data or to transfer the recorded data to an additional computer using network functionality built into the system for further analysis and storage is built into the system.

Because the embodiments as disclosed herein are tablet based, they are portable, cheap and accessible to virtually anyone in the world. The embodiments are simple and intuitive to use and requires minimal maintenance. The embodiments provide objective measurements of cognitive function, are minimally dependent on language, and require only that subjects can point. The embodiments are thus applicable across a very broad age range from young children to seniors. The two pointing tests probe specific brain functions with very high sensitivity. The Pro-Point test probes automatic brain functions whereas the Anti-Point test probes cognitive or willful brain functions. The Pro-Point test also serves as a control for basic sensory motor and general alertness functions.

It is important to note that over the years there are many variants of eye movement tasks, such as a delayed remembered antisaccade, that can be implemented by use of our methods and systems as well to obtain measures of cognitive control and memory. While the Pro-Point and Anti-Point tests are exemplified as a means of measuring stimulus response, other different or additional visual tasks or stimuli could be presented in many different fashions, but ultimately, one would still be measuring response time in accordance with our invention. As a non-limiting example, in a variation of our Pro-Touch and Anti-Touch tests, we developed other simple tasks, for example tasks of reflexive and voluntary social attention that momentarily flash a figure of a head with eyes pointing left or right while the center dot is touched before the second visual stimulus is presented to a target location but otherwise using the same methods and systems measuring response times.

Tests of Device to Detect Mild Concussion from Heading by Young Soccer Players

In this example, embodiments of the invention were successfully used to detect mild cognitive deficits in soccer players after ball heading. In this study the accuracy and speed of automatic (using Pro-Point test) and willful pointing (using Anti-point test) were compared in two groups of high-school subjects: Soccer players and Non-soccer players. The testing was performed on the soccer field demonstrating the portability and field applicability of the system. Further, the testing was performed by a high-school student with supervision, which demonstrates the simplicity of the system. It was found that the accuracy in both types of pointing responses was identical in the two groups. In addition, the speed of automatic pointing was also identical in the two groups. However, the speed of willful pointing differed significantly in the two groups: soccer players were slower than non-soccer players. Further, it was found that the speed of willful responses marginally depended on the number of ball headings and significantly depended on hours of soccer played per week and years of experience. Together, these results confirm the ability of the system to detect subtle but significant changes in cognitive functions in humans.

Studies on Concussion from Heading in Soccer Players Prior to Ours Did not Detect Mild Concussions Concussive brain injuries in head jarring sports such as American football, hockey, and boxing, where repeated loss of consciousness often occur, could lead to long-term cognitive dysfunctions1. However, whether less violent head impacts such as heading a soccer ball could lead to subconcussive brain injury is unclear 2-4. A recent imaging study5 showed detectable structural differences in brain areas, consistent with traumatic brain injury (TBI), between amateur adult (mean age of 31 yrs., played soccer since childhood) soccer players with self-reported high and low heading frequencies. Similar findings were also obtained in another recent imaging study 6 which found differences in white matter integrity in a small sample of professional male soccer players (mean age of 20 yrs., who played soccer since childhood) compared with a control group of swimmers (mean age of 21 yrs.). Previous imaging studies have failed to find structural brain differences directly related to heading balls 7-10. Previous studies using formal cognitive testing have also failed to detect changes with ball heading in young adults 11 or in 13- to 16-year-old soccer players.

Frontal lobes are among the brain regions most susceptible to injury in traumatic brain injury15. Previous studies that did not find significant changes in higher level cognitive tasks associated with soccer ball heading 10,11 have often tested for cognitive changes using more formal but complicated cognitive testing (e.g., visual memory retention, addition, logic, and other tasks that occur at the level of seconds and minutes). We used the new touch based method described above, with tasks similar to those used in eye tracking research, which are simple, straightforward, and less sensitive to interfering issues such as second language differences system, to test to detect the cognitive effects of soccer ball heading by a small sample of young girls of high school age. Our method with its relatively short response latencies and high temporal resolution may be a more sensitive test of executive function and hence be able to detect more subtle cognitive changes in high school soccer players, deficits that were previously undetected because of lack of sensitive measurement techniques.

Methods

The participants were 12 female soccer and 12 female non-soccer players in a high school (median age for both groups=16.5 years; range for both groups was 15-18 years). Both soccer and non-soccer players were recruited through the high school, and a research assistant explained the study to them. The high school was supportive of the study but wanted to minimize any inconvenience to the students, their parents (for minors under 18), and their sports schedule. The soccer sessions were actual varsity training sessions that were on their own tight schedule and it was not possible to run a pre-practice control. The varsity coach controlled the practice, including the heading portion, and we did not have control over what soccer related activity the players performed.

All participants gave informed consent or assent with parental consent and the study was approved by the University of Texas at Houston Committee for the Protection of Human Subjects in accordance with the Declaration of Helsinki. In addition, the study was also approved by the administration of the high school as well as the coaches.

Every soccer player performed head balls during the practice session before the testing, with median 6 (range: 2-20) head balls per session based on self-reports. Data for two of the soccer subjects were not included in the descriptive statistics of heading ball rate or used for the analysis of this variable as their answers were qualitative. No participant in the non-soccer group performed a head ball before testing. The medians (and ranges) for years of soccer playing and current weekly hours of soccer playing were respectively 8 years (range: 5-12) and 11 hours (range: 2-16), for soccer players and 0 and 0 for non-soccer players. The non-soccer players were recruited similar to soccer players with the additional inclusion criteria that they were not currently active in a contact sport and that their age and grade level was matched to the soccer players. All participants had normal or corrected-to-normal vision and none reported any previous head injury nor any other known neurological conditions. The medians for the numbers of hours of video (electronic) game playing were 4.0 and 2.5 hours for soccer and non-soccer players. Eleven of the twelve participants in both the soccer and non-soccer groups were right handed.

Stimuli.

The experiment was performed on an iPad 2 (FIG. 1) with a video frame refresh rate of 60 Hz. The onset and offset of stimuli were synchronized with the frame refresh signal with a precision of 1.6 msec 23. The visual display consisted of a filled center fixation circle (diameter subtending 2.4° visual angle from a 33 cm viewing distance, 1.4 cm) surrounded by four square boxes (1.4°, 0.8 cm) 7.0° (4.0 cm) from the fixation circle indicating possible response locations. Participants started a trial by placing their index finger on the center circle. A visual target (white square, 0.8 cm) appeared randomly 480 ms later, at one of the four locations. For the Pro-Point task, the participant was instructed to touch the response box containing the target as fast as possible without making errors. For the Anti-Point task, the participant was to touch the response box opposite to the target location.

Touch Responses.

The spatial locations of the touches were captured by the iPad's capacitive touch screen and exact coordinates calculated using its touch-screen interface with resolution of 52 pixels per cm. A response was counted as an error if the distance between the target location and the iPad-calculated location was greater than 3.3° (1.9 cm). As described above, the touch screen alone cannot be used for high temporal resolution measurements because of the inherent delay associated with sensing touch via a capacitive screen as well as the fact that these events are then discretized to the frame refresh rate of 60 Hz. A temporal resolution of 0.2 msec can be achieved by using the built-in microphone (44.1 kHz sampling rate) on the iPad to record the vibrations produced by touch onset and offset 23.

Design and Procedure.

The dependent variables were: (1) Initiation Time—the duration between when the visual cue appears and when the finger is lifted, (2) Movement Time—the duration between when the visual cue appears and when the target goal (at the cue or opposite of the cue location) is touched, (3) Total Time—sum of Initiation Time and Movement Time, and (4) Error—when the finger touched more than 3.3° (1.9 cm) from the target goal center. Each participant performed two blocks of trials until they obtained 48 correct trials in each Pro-Point and Anti-Point block (mean total trials 48.3 and 49.4, respectively). Within each participant group, half started with the Pro-Point block followed by the Anti-Point block, and the other half received the reversed order. Both groups were tested after school academic activities were over. Soccer players went to practice right after school academic activities and then were tested in the field immediately following their afternoon practice. To match the environmental conditions, Non-soccer players were also tested outdoors after school academic activities were over at approximately the same time in the afternoon (4-5 pm).

Analysis.

Error trials were excluded from the analyses of response times. Outlier trials with times more than 2.5 SD away from the mean of each subject for each task were excluded iteratively until all remaining trials were within 2.5 SD, removing, for initiation times, 6.86% (Pro-Point) and 3.91% (Anti-Point) and, for movement times, an additional 0.95% and 2.60% of the total trials, respectively. A mixed effect model was performed for response time data and a logit-link generalized linear model with repeated measurements for error data. The logit-link transforms error percentage, p, to logit(p) by log [p/(1−p)]. All models assumed that measurements obtained within each subject have an autoregressive correlation structure, AR(1). Group (soccer vs. non-soccer players) was the between-subject variable for each task (Pro-Point and Anti-Point) and group difference was calculated and tested by constructing the contrasts from the mixed effect models or logit-link generalized linear model. In addition, to test if the Anti-Point response time slowing in the soccer group found in the first group analysis was related to ball heading, years of soccer, or current weekly hours of soccer playing, we performed a similar mixed effect model (with repeated measurements and autoregressive correlation structure) on the Anti-Point response time data from the soccer players with the independent variables of heading rate (n=10), years of soccer playing (n=12), and hours of soccer per week (n=12). Due to missing data, analyses were run separately. Data were analyzed using a significance level of $p<0.05$ and a marginal significance level of $0.05 \leq p < 0.10$.

Results

Figure 8:
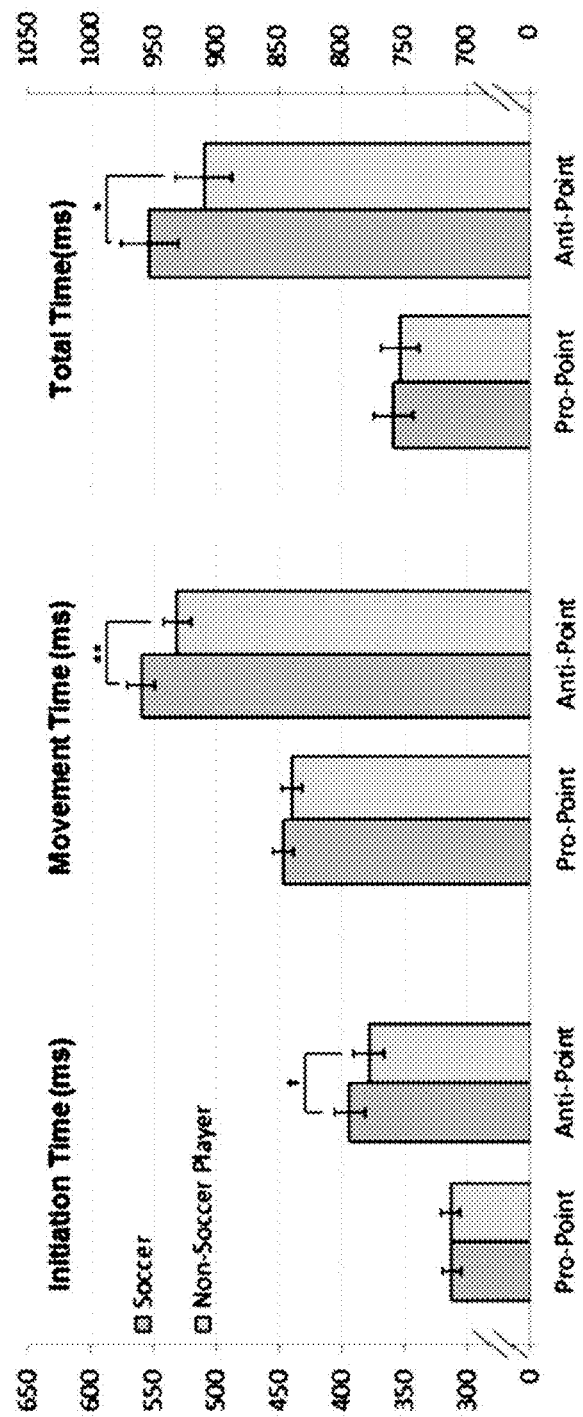
FIG. 8 is estimated mean initiation, movement, and total reaction times for soccer and non-soccer subjects as explained in a test of embodiments.

FIG. 8 shows estimated mean initiation, movement, and total reaction times for soccer and non-soccer subjects Darker bars represent data from soccer players, and lighter bars represent data from non-soccer players. Error bars indicate the 95% confidence interval (d.f.=11). Note that the scale for total time (far right) is different from that of the initiation and movement times. Significance levels: (t) for $p<0.1$, (*) for $p<0.01$, and (**) for $p<0.005$ 14 illustrates mean initiation, movement, and total times to respond to the target as a function of task for both groups. In Pro-Point, there were no differences between soccer and non-soccer players for initiation times (312 ms vs. 313 ms, t(22)=0.16, p=0.87), movement times (445 ms vs. 439 ms, t(22)=1.18, p=0.25), or total times (757 ms vs. 752 ms, t(22)=0.55, p=0.59) using the mixed effect model. In contrast, in Anti-Point, soccer players were marginally slower than non-soccer players for initiation times (394 ms vs. 378 ms, t(22)=1.86, p=0.08) and significantly slower than non-soccer players for movement times (561 ms vs. 531 ms, t(22)=3.69, p<0.005) and total times (955 ms vs. 909 ms, t(22)=2.81, p=0.01) using the mixed effect model.

To further test if Anti-Point response times in soccer players could be accounted for by heading frequency or soccer experience, we included these three variables as independent variables. The mixed effect model with heading ball rate as the independent variable showed marginal effects of heading ball rate for initiation time (t(8)=1.88, p<0.10) and total time (t(8)=1.86, p<0.10), but not movement time (t(8)=1.67, p>0.11) in the Anti-Point task, indicating marginally slower responses with increased number of head balls. With hours of soccer per week as the independent variable, the mixed effect model showed significant effects for Anti-Point task initiation time (t(10)=3.51, p<0.01), movement time (t(10)=2.27, p<0.05) and total time (t(10)=2.95, p<0.02), indicating slower responses with increased hours of soccer per week. Thirdly, with years of soccer as the independent variable, the mixed effect model showed a marginal effect for Anti-Point task initiation time (t(10)=2.94, p<0.07) and significant effects for movement time (t(10)=3.43, p<0.01) as well as total time (t(10)=2.71, p<0.03), indicating slower responses with increased years of soccer experience. Finally, it was determined that the independent variables of heading ball rate, hours of soccer played per week, and years of soccer played were unrelated/uncorrelated by Pearson correlation coefficients.

There were no significant differences in errors in either Pro-Point tasks (0.3% vs. 1.0%, z=0.83, p=0.41, logit-link generalized model) or Anti-Point (3.1% vs. 2.5%, z=1.13, p=0.26, for soccer and non-soccer players, logit-link generalized model).

Conclusion of Tests Using Embodiment

The results show that soccer playing in which participants headed the ball did indeed disrupt voluntary performance in female high school soccer players tested immediately following practice. In addition, even in this small sample, this response time slowing on the Anti-Point task was marginally related to number of ball headers (n=10) and significantly related to hours of soccer per week (n=12) and years of soccer playing (n=12). We found no evidence that slowing occurred during reflexive movements under identical sensorimotor conditions (Pro-Point). These findings demonstrate significant and specific cognitive changes in female high school soccer players who head the soccer ball during practice.

Though the changes we report were robust, they do not necessarily imply sustained changes or brain injury. To our knowledge, these results provide the first evidence that even subconcussive blows in soccer could lead to measurable, even if possibly transient, cognitive changes in young soccer players.

In sum, the cognitive changes that we report were measured with an embodiment comprising a simple iPad based application. A simple tool such as this embodiment involving an iPad application may be a quick and effective method to screen for and track cognitive deficits in sports players. It could potentially be used to detect, screen, and track other populations for mild traumatic brain injury and development of cognitive comorbidities.

The tests are very simple and are minimally sensitive to language and age requirements. The system does not require a special or controlled environment, training for administration, or scoring by trained personnel or specialist. Further, the tablet platform on which the tests run is extremely simple to use and maintain. Everything that is needed to test an individual and to transfer the recorded data to an additional computer is built into the device.

In the foregoing specification, the invention has been described with reference to specific embodiments. However, one of ordinary skill in the art appreciates that various modifications and changes can be made without departing from the scope of the invention. Accordingly, the specification and figures are to be regarded in an illustrative rather than a restrictive sense, and all such modifications are intended to be included within the scope of invention.

Although the invention has been described with respect to specific embodiments thereof, these embodiments are merely illustrative, and not restrictive of the invention. The description herein of illustrated embodiments of the invention is not intended to be exhaustive or to limit the invention to the precise forms disclosed herein (and in particular, the inclusion of any particular embodiment, feature or function is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment," "an embodiment," or "a specific embodiment" or similar terminology means that a particular feature, structure, or characteristic described in connection with the embodiment is included in at least one embodiment and may not necessarily be present in all embodiments. Thus, respective appearances of the phrases "in one embodiment," "in an embodiment," or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Any suitable programming language can be used to implement the routines, methods or programs of embodiments of the invention described herein, including C, C++, Java, assembly language, etc. Different programming techniques can be employed such as procedural or object oriented. Any particular routine can execute on a single computer-processing device or multiple computer processing devices, a single computer processor or multiple computer processors. Data may be stored in a single storage medium or distributed through multiple storage mediums, and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps and operations described herein can be performed in hardware, software, firmware or any combination thereof.

Embodiments described herein can be implemented in the form of control logic in software or hardware or a combination of both. The control logic may be stored in an information storage medium, such as a computer-readable medium, as a plurality of instructions adapted to direct an information-processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or of the steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more general purpose digital computers, by using application specific integrated circuits, programmable logic devices, field programmable gate arrays, optical, chemical, biological, quantum or nano-engineered systems, components and mechanisms may be used. In general, the functions of the invention can be achieved by any means as is known in the art. For example, distributed, or networked systems, components and circuits can be used. In another example, communication or transfer (or otherwise moving from one place to another) of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

PUBLICATIONS CITED

1. Kelly J C, Amerson E H, Barth J T (2012) *Mild traumatic brain injury: Lessons learned from clinical, sports, and combat concussions.* Rehabilitation Research and Practice 2012: 5 pages.
2. Rutherford A, Stephens R, Potter D (2003) *The neuropsychology of heading and head trauma in Association Football (soccer): a review.* Neuropsychol Rev 13.
3. Kirkendall D T, Jordan S E, E. G W (2001) *Heading and head injuries in soccer.* Sports Med 31:369-386.
4. Matser E J, Kessels A G, Lezak M D, Jordan B D, Troost J (1999) *Neuropsychological impairment in amateur soccer players.* Journal of American Medical Association 282:971-973.
5. Kim N, Zimmerman M, Lipton R, Stewart W, Gulko E, et al. *Making Soccer Safer for the Brain: DTI-defined Exposure Thresholds for White Matter Injury Due to Soccer Heading* 2011; McCormick Place, Chicago, USA.
6. Koerte I K, Ertl-Wagner B, Zafonte R, Shenton M E (2012) *White matter integrity in the brains of professional soccer players without a symptomatic concession.* Journal of American Medical Association 308:1859-1861.
7. Autti T, Sipila L, Autti H, Salonen O (1997) *Brain lesions in players of contact sports.* Lancet 349:1144.
8. Haglund Y, Ericsson E (1993) *Does amateur boxing lead to chronic brain damage? A review of recent investigations.* Am J Sports Med 21: 97-107.
9. Jordan S, Green E, Galantly H, Mandelbaum B, Jabour B (1996) *Acute and chronic brain injury in United States National Team Football Players.* Am J Sports Med 24:205-210.
10. Stephens R, Rutherford A, Potter D, Fernie G (2010) *Neuropsychological consequence of soccer play in adolescent U.K. school team soccer players.* Journal of Neuropsychiatry and Clinical Neuroscience 22:295-303.
11. Rieder C, Jansen P (2011) *No neuropsychological consequence in male and female soccer players after a short heading training.* Arch Clin Neuropsychol 26: 583-591.
12. Hill S K, Reilly J L, Harris M S, Khine T, Sweeney J A (2008) *Oculomotor and neuropsychological effects of antipsychotic treatment for schizophrenia.* Schizophr Bull 34:494-506.
13. Broerse A, Holthausen E A, van den Bosch R J, den Boer J A (2001) *Does frontal normality exist in schizophrenia? A saccadic eye movement study.* Psychiatry Res 103:167-178.
14. Gooding D C, Mohapatra L, Shea H B (2004) *Temporal stability of saccadic task performance in schizophrenia and bipolar patients.* Psychol Med 34:921-932.
15. Wilde E A, Hunter J V, Newsome M R, Scheibel R S, Bigler E D, et al. (2005) *Frontal and temporal morphometric findings on MRI in children after moderate to severe traumatic brain injury.* J Neurotrauma 22:333-344.
16. Sereno A B, Holzman P S (1995) *Antisaccades and Smooth Pursuit Eye Movement Function in Schizophrenia.* Biological Psychiatry 37: 394-401.
17. Sereno A B, Babin S L, Hood A J, Jeter C B (2009) *Executive Functions: Eye Movements and Neuropsychiatric Disorders.* Encyclopedia of Neuroscience 4:117-122.
18. Munoz D P, Evening S (2004) *Look away: the antisaccade task and the voluntary control of eye movement.* Nat Rev Neurosci 5: 218-228.
19. Everting S, Fischer B (1998) *The antisaccade: a review of basic research and clinical studies.* Neuropsychologia 36: 885-899.
20. Khatoon S, Briand K A, Sereno A B (2002) *The role of response in spatial attention: Direct versus indirect stimulus-response mappings.* Vision Research 42: 2693-2708.
21. Wise S P, Murray E A (2000) *Arbitrary associations between antecedents and actions.* Trends Neurosci 23: 271-276.
22. Toni I, Rushworth M F, Passingham R E (2001) *Neural correlates of visuomotor associations. Spatial rules compared with arbitrary rules.* Exp Brain Res 141: 359-369.
23. Shrestha Y, Thomas M S, Red S, Patel S S, Sereno A B. *A tablet based stimulus and response system for cognitive and behavioral experiments;* 2011. pp. 64.
24. Audiffren M, Tomporowski P D, Zagrodnik J (2008) *Acute aerobic exercise and information processing: Energizing motor processes during a choice reaction time task.* Acta Psychologica 129:410-419.
25. Lambourne K, Tomporowski P (2010) *The effect of exercise-induced arousal on cognitive task performance: A meta-regression analysis.* Brain Research 1341:12-24.
26. Matser J T, Kessels A G, Lezak M D, Troost J (2001) *A dose-response relation of headers and concussions with cognitive impairment in professional soccer players.* J Clin Exp Neuropsychol 23.
27. Witol A D, Webbe F M (2003) *Soccer heading frequency predicts neuropsychological deficits.* Arch Clin Neuropsychol 18: 397-417.
28. Kontos A P, Dolese A, Elbin R J, Covassin T, Warren B L (2011) *Relationship of soccer heading to computerized neurocognitive performance and symptoms among female and male youth soccer players.* Brain Inj 25:1234-1241.
29. Kaminski T W, Wikstrom A M, Gutierrez G M, Glutting J J (2007) *Purposeful heading during a season does not influence cognitive function or balance in female soccer players.* J Clin Exp Neuropsychol 2007 Feb. 22: 1-10 [Epub ahead of print] February 22: 1-10.

The invention claimed is:

1. A method of measuring user reaction times to a visual stimulus on a portable touch screen device having a capacitive touch-sensitive surface with a touch reporting mechanism, and one or more modules at least partially implemented in software, said one or more modules being responsive to a user start command to
   a) open a time log file on receipt of said start command,
   b) generate a visual stimulus at a first location on the touch screen surface for touch by a user,
   c) generate at least one second visual stimulus at a second location on the touch screen surface spaced from said first location and write time of generation of the second visual stimulus to a log file signifying such time of generation (Tv),
   d) receive notification of capacitance sensed touch and coordinates of such sensed touch and write timer time to a log file (Tc) signifying time of such sensed touch and also write the sensed touch coordinates location to a file,
   e) remove the second visual stimulus from the touch screen surface, steps b)-e) comprising a single trial,
   f) repeat steps b)-e) until a set of trials signified by a predetermined number of capacitance sensed touches (Tc) of said second location attains a preset number, then cease repeating steps b)-e), and close the log file onto a computer readable medium which may be in said device or in communication with said device, and
   g) in a computing device which may be the same as said portable device or another computing device having one or more modules implemented at least partially in software and to which the data from said portable device is transmitted, determine a user reaction time (RT) by
1) opening the log file from step f),
2) reading the data from the log file corresponding to Tc for each trial,
3) calculating uncorrected response time: RTuncorrected=Tc−Tv for each trial,
4) calculating response time corrected for accuracy: RTaccuracy corrected=RTuncorrected−Kc, where Kc is an empirically measured constant corresponding to the average latency of the capacitive touch reporting mechanism, and
5) writing the accuracy corrected response time to an output.

2. A system comprising one or more modules at least partially implemented in software and configured to measure user reaction times to a visual stimulus on a portable touch screen device having a capacitive touch-sensitive surface with a touch reporting mechanism, said one or more modules being responsive to a user start command to:
a) open a time log file on receipt of said start command,
b) generate a visual stimulus at a first location on the touch screen surface for touch by a user,
c) generate at least one second visual stimulus at a second location on the touch screen surface spaced from said first location and write time of generation of the second visual stimulus to a log file signifying such time of generation (Tv),
d) receive notification of capacitance sensed touch and coordinates of such sensed touch and write timer time to a log file (Tc) signifying time of such sensed touch and also write the sensed touch coordinates location to a file,
e) remove the second visual stimulus from the touch screen surface, steps b)-e) comprising a single trial,
f) repeat steps b)-e) until a set of trials signified by a predetermined number of capacitance sensed touches (Tc) of said second location attains a preset number, then cease repeating steps b)-e), and close the log file onto a computer readable medium which may be in said device or in communication with said device, and
g) in a computing device, which may be the same as said portable device or another computing device having one or more modules implemented at least partially in software and to which the data from said portable device is transmitted, determine a user reaction time (RT) by
1) opening the log file from step f),
2) reading the data from the log file corresponding to Tc for each trial,
3) calculating uncorrected response time: RTuncorrected=Tc−Tv for each trial,
4) calculating response time corrected for accuracy: RTaccuracy corrected=RTuncorrected−Kc where Kc is an empirically measured constant corresponding to the average latency of the capacitive touch reporting mechanism, and
5) writing the accuracy corrected response time to an output.

3. A method of measuring user reaction times to a visual stimulus on a portable touch screen device having a capacitive touch-sensitive surface with a touch reporting mechanism, and one or more modules at least partially implemented in software, said one or more modules being responsive to a user start command, as claimed in claim 1 further comprising:

1) coincident with step a), commence recording for input signals from an acoustic sensor to an audio file and write a timer time to a log file signifying a time of a start of this monitoring (Ta),
2) in step f), close said audio and log files onto a computer readable medium which may be in said device or in communication with said device upon completion of the set of trials for steps b)-e),
3) in step g, determine a user reaction time by:
1) opening the audio file in addition to the log file from step f),
2) completion of steps 2)-4) of step q),
3) determining an audio sample from the audio file corresponding to a touch response from a touch sensor (Nc) and convert it to time (Tc+Ka),
4) defining a time window as Tc+Ka−t1 to Tc+Ka+t2 to search for audio signatures of touch in the audio file for each trial, where t1 and t2 are fixed durations for said device,
5) reading audio samples from the audio file corresponding to a search window defined as $N_L$ to $N_U$,
6) locating audio samples corresponding to maximum amplitude (Nmax) and converting said maximum amplitude to time (Tmax),
7) calculating Wmax=Tmax−(Tc−Ta−t1),
8) calculating an audio based correction of dt=Wmax−Mean(Wmax), where Mean(Wmax) is the Wmax averaged across all the trials comprising steps a)-f),
9) calculating a precision corrected response time RTcorrected=RTaccuracycorrected+dt, and
10) writing RTcorrected to an output in addition to writing the accuracy corrected response time to an output in step 5) of step q.

4. A method comprising one or more modules at least partially implemented in software and configured to measure user reaction times to visual stimulus on a portable touch screen device having a capacitive touch-sensitive surface with a touch reporting mechanism, an acoustic sensor proximal to said surface, said one or more modules being responsive to a user start command, as claimed in claim 1 further comprising measurement chosen from one of the following: Kc or RTcorrected from signals derived from the acoustic sensor as below:
1) coincident with step a), commence recording for input signals from an acoustic sensor to an audio file and write a timer time to a log file signifying a time of a start of this monitoring (Ta),
2) in step c), convert the at least one second visual stimulus to a vibration using a photo detector and a sound or vibration source proximal to said surface,
3) in step f), close said audio and log files onto a computer readable medium which may be in said device or in communication with said device upon completion of the set of trials for steps b)-e),
4) for each trial, comprising of steps b)-e), calculate the accurate and precise response time RTcorrected, from the audio file, by taking a difference between the onset time of two acoustic sensor signals: a signal indicating the onset of the at least one second visual stimulus and a signal indicating the onset of a touch response,
5) computing Kc by regressing RTuncorrected from step 3) of step q) against RTcorrected as below:
a) RTcorrected=RTuncorrected+Kc,
6) storing Kc onto a computer readable medium which may be in said device or in communication with said device for correcting timing of touch responses when not using a light to sound/vibration converter, and 7) writing RTcorrected to an output file as a precise and accurate timing of touch responses when using a light to sound/vibration converter and storing an output file onto a computer readable medium which may be in said device or in communication with said device.

5. A system of measuring user reaction times to a visual stimulus on a portable touch screen device having a capacitive touch-sensitive surface with a touch reporting mechanism, and one or more modules at least partially implemented in software, said one or more modules being responsive to a user start command, as claimed in claim 2 further comprising:
1) coincident with step a), commence recording for input signals from an acoustic sensor to an audio file and write a timer time to a log file signifying a time of a start of this monitoring (Ta),
2) in step f), close said audio and log files onto a computer readable medium which may be in said device or in communication with said device upon completion of the set of trials for steps b)-e), and
3) in step g, determine a user reaction time by:
    1) opening the audio file in addition to the log file from step f),
    2) completion of steps g) 2)-4),
    3) determining an audio sample from the audio file corresponding to a touch response from a touch sensor (Nc) and convert it to time (Tc+Ka),
    4) defining a time window as Tc+Ka−t1 to Tc+Ka+t2 to search for audio signatures of touch in the audio file for each trial, where t1 and t2 are fixed durations for said device,
    5) reading audio samples from the audio file corresponding to a search window defined as $N_L$ to $N_U$,
    6) locating audio samples corresponding to maximum amplitude (Nmax) and converting said maximum amplitude to time (Tmax),
    7) calculating Wmax=Tmax−(Tc−Ta−t1),
    8) calculating an audio based correction of dt=Wmax−Mean(Wmax), where Mean(Wmax) is the Wmax averaged across all the trials comprising steps a)-f),
    9) calculating a precision corrected response time RTcorrected=RTaccuracycorrected+dt, and
    10) writing RTcorrected to an output in addition to writing the accuracy corrected response time to an output in step g)5).

6. A system comprising one or more modules at least partially implemented in software and configured to measure user reaction times to visual stimulus on a portable touch screen device having a capacitive touch-sensitive surface with a touch reporting mechanism, an acoustic sensor proximal to said surface, said one or more modules being responsive to a user start command, as claimed in claim 2 further comprising measurement chosen from one of the following: Kc or RTcorrected from signals derived from the acoustic sensor as below:
1) coincident with step a), commence recording for input signals from an acoustic sensor to an audio file and write a timer time to a log file signifying a time of a start of this monitoring (Ta),
2) in step c), instantly convert the at least one second visual stimulus to a vibration using a photo detector and a sound or vibration source proximal to said surface,
3) in step f), close said audio and log files onto a computer readable medium which may be in said device or in communication with said device upon completion of the set of trials for steps b)-e),
4) for each trial, comprising of steps b-e, calculate the accurate and precise response time RTcorrected, from the audio file, by taking a difference between the onset time of two acoustic sensor signals: the signal indicating an onset of at least one second visual stimulus and second signal indicating the onset of a touch response,
5) computing Kc by regressing RTuncorrected from step 3) of step g) against RTcorrected as below:
    a. RTcorrected=RTuncorrected+Kc,
6) storing Kc onto a computer readable medium which may be in said device or in communication with said device for correcting timing of touch responses when not using the light to sound/vibration converter, and
7) writing RTcorrected to an output file as a precise and accurate timing of touch responses when using a light to sound/vibration convertor and storing an output file onto a computer readable medium which may be in said device or in communication with said device.

* * * * *